(12) United States Patent
Periana et al.

US010745340B2

(10) Patent No.: US 10,745,340 B2
(45) Date of Patent: Aug. 18, 2020

(54) OXIDATION OF ALKANES TO ALCOHOLS

(71) Applicant: The Scripps Research Institute, La Jolla, CA (US)

(72) Inventors: Roy A Periana, Jupiter, FL (US); Brian G Hashiguchi, Palm Beach Gardens, FL (US); Michael M Konnick, Palm Beach Gardens, FL (US); Steven M Bischof, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 3 days.

(21) Appl. No.: 14/770,039

(22) PCT Filed: Feb. 25, 2014

(86) PCT No.: PCT/US2014/018175
§ 371 (c)(1),
(2) Date: Aug. 24, 2015

(87) PCT Pub. No.: WO2014/130987
PCT Pub. Date: Aug. 28, 2014

(65) Prior Publication Data
US 2016/0002139 A1    Jan. 7, 2016

Related U.S. Application Data

(60) Provisional application No. 61/768,715, filed on Feb. 25, 2013, provisional application No. 61/862,715, filed on Aug. 6, 2013, provisional application No. 61/862,723, filed on Aug. 6, 2013, provisional application No. 61/862,731, filed on Aug. 6, 2013.

(51) Int. Cl.
*C07C 67/035* (2006.01)

(52) U.S. Cl.
CPC .................. *C07C 67/035* (2013.01)

(58) Field of Classification Search
CPC .................................. C07C 67/035
USPC .................................. 560/131, 227
See application file for complete search history.

(56) References Cited

U.S. PATENT DOCUMENTS

| 4,038,322 | A | * | 7/1977 | DE Radzitzky d'Ostrowick ........ C07C 29/48 560/241 |
|---|---|---|---|---|
| 4,113,756 | A | | 9/1978 | Johnson |
| 4,192,814 | A | | 3/1980 | Johnson |
| 5,008,420 | A | * | 4/1991 | Greco .................... C01F 7/162 556/181 |
| 2002/0103402 | A1 | * | 8/2002 | Chang .................... C07C 27/16 568/671 |
| 2005/0161342 | A1 | | 7/2005 | Carson et al. |
| 2007/0149832 | A1 | * | 6/2007 | Chen .................... C07C 29/095 568/910 |
| 2007/0149833 | A1 | | 6/2007 | Brandvold et al. |
| 2008/0164443 | A1 | | 7/2008 | White et al. |
| 2009/0062558 | A1 | * | 3/2009 | Sander .................. C07C 17/208 552/625 |
| 2009/0203944 | A1 | | 8/2009 | An et al. |
| 2009/0234121 | A1 | | 9/2009 | Periana et al. |
| 2013/0261348 | A1 | * | 10/2013 | Scates .................. C07C 29/141 568/881 |

FOREIGN PATENT DOCUMENTS

| CN | 102161614 A | * | 8/2011 |
|---|---|---|---|
| WO | WO 1992/014738 A1 | | 9/1992 |

OTHER PUBLICATIONS

Periana et al reference (Science (1993), vol. 259, No. 5093, pp. 340-343) (Year: 1993).*
European Patent Office, European Extended Search Report for EP Appln. 14753994.4 (dated Feb. 22, 2016), 7 pgs.
Hashiguchi, et al., Accounts of Chemical Research, 45 (6) (Apr. 6, 2012) pp. 885-898.
International Search Report and Written Opinion from PCT Application No. PCT/US2014/018175 (dated May 22, 2014).
Himmel et al., "A Unified pH Scale for All Phases," *Angew. Chem. Int. Ed.*, 49(38): 6885-6888 (2010).

* cited by examiner

*Primary Examiner* — Shaojia A Jiang
*Assistant Examiner* — Everett White
(74) *Attorney, Agent, or Firm* — Leydig, Voit & Mayer, Ltd.

(57) ABSTRACT

The invention provides processes and materials for the efficient and cost-effective functionalization of alkanes, such as methane from natural gas, to provide esters, alcohols, and other compounds. The method can be used to produce liquid fuels such as methanol from a natural gas methane-containing feedstock. The soft oxidizing electrophile, a compound of a main group, post-transitional element such as Tl, Pb, Bi, and I, that reacts to activate the alkane C—H bond can be regenerated using inexpensive regenerants such as hydrogen peroxide, oxygen, halogens, nitric acid, etc. Main group compounds useful for carrying out this reaction includes haloacetate salts of metals having a pair of available oxidation states, such as Tl, Pb, Bi, and I. The inventors herein believe that a unifying feature of many of the MXn electrophiles useful in carrying out this reaction, such as Tl, Pb, and Bi species, is their isoelectronic configuration in the alkane-reactive oxidation state; the electrons having the configuration [Xe]4f145d10, with an empty 6s orbital. However, the iodine reagents have a different electronic configuration.

21 Claims, 8 Drawing Sheets

OXIDATION OF ALKANES TO ALCOHOLS

CROSS-REFERENCE TO RELATED APPLICATIONS

This application is a U.S. national phase of International Patent Application No. PCT/US2014/018175, filed Feb. 25, 2014, which claims the benefit of U.S. Provisional Application Nos. 61/768,715, filed Feb. 25, 2013; 61/862,715, filed Aug. 6, 2013; 61/862,723, filed Aug. 6, 2013; and 61/862,731, filed Aug. 6, 2013, which applications are incorporated by reference herein in their entireties.

STATEMENT OF GOVERNMENT SUPPORT

This invention was made with government support under GQ10044-133945 awarded by the U.S. Department of Energy. The government has certain rights in the invention.

BACKGROUND

Natural gas (NG) is becoming an increasingly abundant resource in the US and around the world.[1] While NG is used for heating it would be ideal to upgrade this resource to chemicals and liquid fuels. This could augment or potentially replace petroleum as the feedstock for chemicals and fuels. Natural gas is also abundantly available in remote locations where transportation to centers of use is not economically viable. In these cases it would be desirable to have an inexpensive process to convert the natural gas to a more easily transported form such as a liquid. However, the existing high-temperature, indirect processes based on the conversion of natural gas to syngas ($CO/H_2$) followed by conversion of the syngas to chemicals and liquid fuels are too energy and capital intensive to economically compete with products from petroleum. Current processes for the conversion of natural gas to fuels and chemicals require high-temperature (>800° C.) to generate synthesis gas or olefins. These processes are very capital and energy intensive and are only economical at very large scales. Therefore, there is a need for economical and environmentally benign processes for production of lower alcohols and other oxygenates from natural gas alkanes. It is generally considered that a direct, lower temperature (<300° C.), selective process to convert the gases in NG (primarily methane, ethane and propane[2]) to liquid products such as alcohols could be used to generate chemicals and liquid fuels at much lower cost than the existing high-temperature, indirect syngas processes.

A technology for the direct low-cost conversion of the major components of natural gas (methane, ethane, propane) to liquid fuels and chemicals such as oxygenates would provide a path to increased value for these sources of natural gas. The potential market for such technology is large; e.g., the global market value for ethylene glycol is over $20 billion/yr with the US at over $4 billion/yr. The markets for other oxygenates such as methanol, ethanol (that can also be inexpensively converted to ethylene), isopropanol, propylene glycol, etc., are also very large. The liquid fuels market is enormous; a 2% penetration of the projected US transportation fuels market, equivalent to the projected annual growth rate in the US, would represent about 50 plants of 14,500 barrel per day capacity.

An important approach that has emerged in the last few decades is the design of molecular (homogeneous) catalysts for the oxidative functionalization of alkanes based on the CH activation reaction. This involves reaction of an M-X catalyst with a hydrocarbon CH bond (R—H) under relatively mild conditions to selectively generate a M-R intermediate that can be converted to the desired R—X product with regeneration of M-X (eq.1).

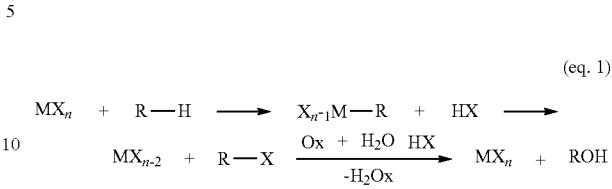

(eq. 1)

There has been significant effort in this area of research with homogeneous[3-23] as well as heterogeneous catalysts[24-26] and substantial progress has been made in recent years. Most of the work on the homogeneous systems have been primarily based on transition metals (with unfilled d-shells, $d^{<10}$) such as Pt,[3,4,16] Pd,[14,17-19,23] Rh,[20-22] and Ir.[7-10] In contrast, relatively few studies have been directed toward the classic main group elements with filled a d-shell ($d^{10}$).

In 1993, we reported an example of a main group, metal cation, $Hg^{II}$, in the superacid solvents, concentrated $H_2SO_4$ and $CF_3SO_3H$, for direct conversion of methane to methanol esters.[15] In spite of the simplicity of the $Hg^{II}$ system, it was not further developed due to lack of reaction in more practical weaker acid media such as $CF_3CO_2H$ (TFAH or HTFA), $CH_3CO_2H$ (HOAc), or aqueous acids where product separation could be practical. Another key issue was that the reactions of ethane and propane were unselective with the $Hg^{II}$ system. We originally proposed an electrophilic CH activation mechanism for the $Hg^{II}$ system. However, later work by Sen based on the observation of products resulting from C—C cleavage reactions with higher alkanes suggested that Hg(II) in superacid media was sufficiently oxidizing to initiate free radical reactions.

This possibility for unselective radical reactions with higher alkanes was also considered by Moiseev and coworkers in the early 1990s in the reaction of methane, ethane, and propane in TFAH with several strongly oxidizing salts that were known to be effective for oxidizing hydrocarbons by free radical mechanisms.[27,28] The initial report showed high yield and selectivity for the stoichiometric reactions of $Co^{III}$ with methane to Me-TFA. Carrying out the reaction with $Co^{II}$ in the presence of $O_2$ showed a TON of ~4 for Me-TFA along with comparable amounts of $CO_2$ generated by solvent decarboxylation. Along with $Co^{IV}$ peroxo species both radical and non-radical mechanisms were considered. In a later report focusing on the reactions of ethane and propane the authors proposed a free radical mechanism to account for the extensive C—C cleavage and over-oxidation reactions with these higher alkanes.

In our own work on $Hg^{II}$ the main group $d^{10}$ cation, $Tl^{III}$ was found to be active for methane oxidation to the ester. However, this was only examined in superacid media and only with methane. As with $Hg^{II}$ this system was likewise inactive in more practical weaker acids. No further work was carried out on the $Tl^{III}$ system in TFAH or with higher alkanes and $Pb^{IV}$ was not examined. The primary basis for this was the recognition that both $Tl^{III}$ (E°=1.2 V) and $Pb^{IV}$ (E°=1.5 V) are stronger oxidants than $Hg^{II}$ (E°=0.9V).[29] Consequently, on the basis of the general considerations at that time, we considered that these main group cations would be more likely than $Hg^{II}$ to initiate unselective radical reaction with the higher alkanes. To our knowledge, since those early publications in 1990's there are no reported, deliberate studies of reactions of higher alkanes with those or other strongly oxidizing main group electrophiles.

SUMMARY

The present invention is directed to compositions and methods for direct oxidation of hydrocarbons, such as methane, ethane, and propane, in a medium that does not include a superacid, wherein a reactive main group element in a compound of formula $MX_n$, such as thallium, lead, bismuth, antimony, selenium, tellurium, or iodine, in an oxidized form or state, is used to generate a reactive intermediate, which in at least some embodiments is derived from electrophilic substitution of an alkane hydrogen atom by the reactive main group element. Other molecular mechanisms may also be operant. The reactive main group element in oxidized form, is termed a soft oxidizing electrophile, although in some embodiments, the reaction may proceed by a mechanism other than electrophilic attack on a C—H bond.

The reaction of the reactive main group element with the alkanes is carried out in an acidic medium, but does not require the presence of a super-acid such as trifluoromethanesulfonic acid or concentrated sulfuric acid. The acidic medium comprises an oxygen acid, e.g., trifluoroacetic acid, acetic acid, methanesulfonic acid, or aqueous solutions thereof, and yields an activated $X_{(n-1)}$M-R intermediate product wherein the main group element has substituted an H of the C—H bond. Without wishing to be bound by theory, the inventors herein believe that in at least many of the embodiments, the main group element has substituted the H of the C—H bond by an electrophilic process. It is also possible that the activated intermediate could be generated by an insertion reaction to the C—H bond. The inventors herein have surprisingly discovered that using the compositions and methods disclosed herein, efficient reaction of an alkane can be achieved without the presence of a superacid, and under relatively mild conditions, e.g., under 300° C., preferably under 200° C., to provide the activated intermediate This activated intermediate $X_{(n-1)}$M-R can then undergo reaction with the solvent milieu, e.g., trifluoroacetic acid, acetic acid, methanesulfonic acid, and the like to provide as an isolable product R—X, a functionalized alkane, the alkyl oxygenate, e.g., an alkyl trifluoroacetate, alkyl acetate, alkyl methanesulfonate, and the like, respectively. The reactive main group element byproduct from this reaction, in a reduced state relative to the reagent used in the initial step, can be recovered and recycled back to its reactive, oxidized, state, by contact with a secondary oxidant, e.g., oxygen gas, peroxide, or the like. If the reaction is carried out in the presence of an oxidant such as $O_2$ or $H_2O_2$ or the like, the reduced form can be reoxidized in situ and the reactive main group element would operate as a catalyst.

The product alkyl oxygenate, e.g., methyl trifluoroacetate, is readily converted to methanol with recovery of the acid, e.g., trifluoroacetic acid, which can be reused in the initial step. Accordingly, both the reactive main group element in oxidized form and the acidic reaction medium can be recycled, such that the net conversion is oxidation of the alkane, with reduction of the secondary oxidant (e.g., $O_2$, hydrogen peroxide) in regeneration of the reactive main group element in oxidized form.

By the methods and compositions disclosed and claimed herein, a viable industrial approach is provided to convert alkanes, e.g., light alkanes such as methane, ethane, and propane from natural gas, to oxygenate products such as alcohols, diols, and the like. The reactive main group element in oxidized form can bring about what is believed by the inventors to be an initial electrophilic C—H bond activation reaction. Or, the reaction can take place by a different mechanism, but yielding a product equivalent to the product of C—H bond insertion reaction, e.g., by radical or insertion mechanisms. After formation of the activated intermediate and conversion to the functionalized alkane, it is possible to recover the reduced form of reagent M for recycling back to the reactive, oxidized state $MX_n$. The reactivity of the reagents and methods disclosed and claimed herein allows the process to be carried out without the presence of an expensive or difficult-to-handle superacid, a hitherto unachieved goal. By the discoveries of the inventors herein a low-temperature, low-pressure, and sustainable process with in situ or ex situ reagent recycling has been devised, that offers an economically and environmentally attractive alternative to the syngas approach to production of lower alcohols such as methanol from lower alkanes on an industrial scale.

Accordingly, the invention provides in various embodiments a process for the oxidation of an alkane to an alkane oxygenate, comprising (a) contacting the alkane and a soft oxidizing electrophile comprising a main group element in oxidized form, or contacting the alkane and a reduced form of the soft oxidizing electrophile plus an oxidant, in an acidic medium comprising an oxygen acid, in the absence of a super-acid, at a temperature of less than 300° C., to provide the alkane oxygenate and an electrophile reduction product; and (b) separating the alkane oxygenate and the electrophile reduction product.

The process can further comprise (c) contacting the separated electrophile reduction product and an oxidizing regeneration reagent, to regenerate the soft oxidizing electrophile.

For example, the soft oxidizing electrophile can comprise the element thallium, lead, bismuth, antimony, selenium, tellurium, or iodine, in oxidized form, which is reduced in the alkane activation step, and can be recovered and regenerated into active form following conversion of the activated alkane to the functionalized alkane oxygenate. The main group, post-transitional metals and non-metals that can be used for the soft oxidizing electrophile can include any of elements 31-35, 49-53, or 81-83. The elements can cycle between a higher oxidation state (in the soft oxidizing electrophile reagent that reacts with the alkane C—H bond) and a lower oxidation state (the electrophile reduction product, from which the soft oxidizing electrophile can be regenerated, either in situ or in a discrete step). By this means, an economically and environmentally favorable self-contained system for alkane conversion to alkane oxygenates can be operated, consuming only a second oxidant, which can be a readily available oxidant such as hydrogen peroxide, oxygen, and the like.

In various embodiments, the oxidizing regeneration reagent is present in at least stoichiometric quantities relative to the alkane, in the acidic medium with the soft oxidizing electrophile, and the oxidizing regeneration reagent oxidizes the electrophile reduction product to the soft oxidizing electrophile in the acidic medium in the presence of the alkane. In such embodiments, the second oxidant serves to regenerate the soft oxidizing electrophile from the electrophile reduction product formed in reaction of the soft oxidizing electrophile with the alkane. For instance, the soft oxidizing electrophile comprising a main group element in oxidized form can be present in less than stoichiometric quantities relative to the alkane and can act as a catalyst. For instance, the oxidizing regeneration reagent can comprise hydrogen peroxide, oxygen, nitric acid, or a halogen.

In other embodiments of the process, no oxidizing regeneration reagent is present in the acidic medium with the soft oxidizing electrophile comprising a main group element in oxidized form, and the soft oxidizing electrophile is present in at least stoichiometric quantities relative to the alkane in the acidic medium. In such embodiments, the electrophile reduction product can be oxidized back to the soft oxidizing electrophile in a discrete step, such as in a two-reactor system that cycles between alkane functionalization and soft oxidizing electrophile regeneration with the second oxidant, discussed in greater detail below.

DETAILED DESCRIPTION

Figure 1:
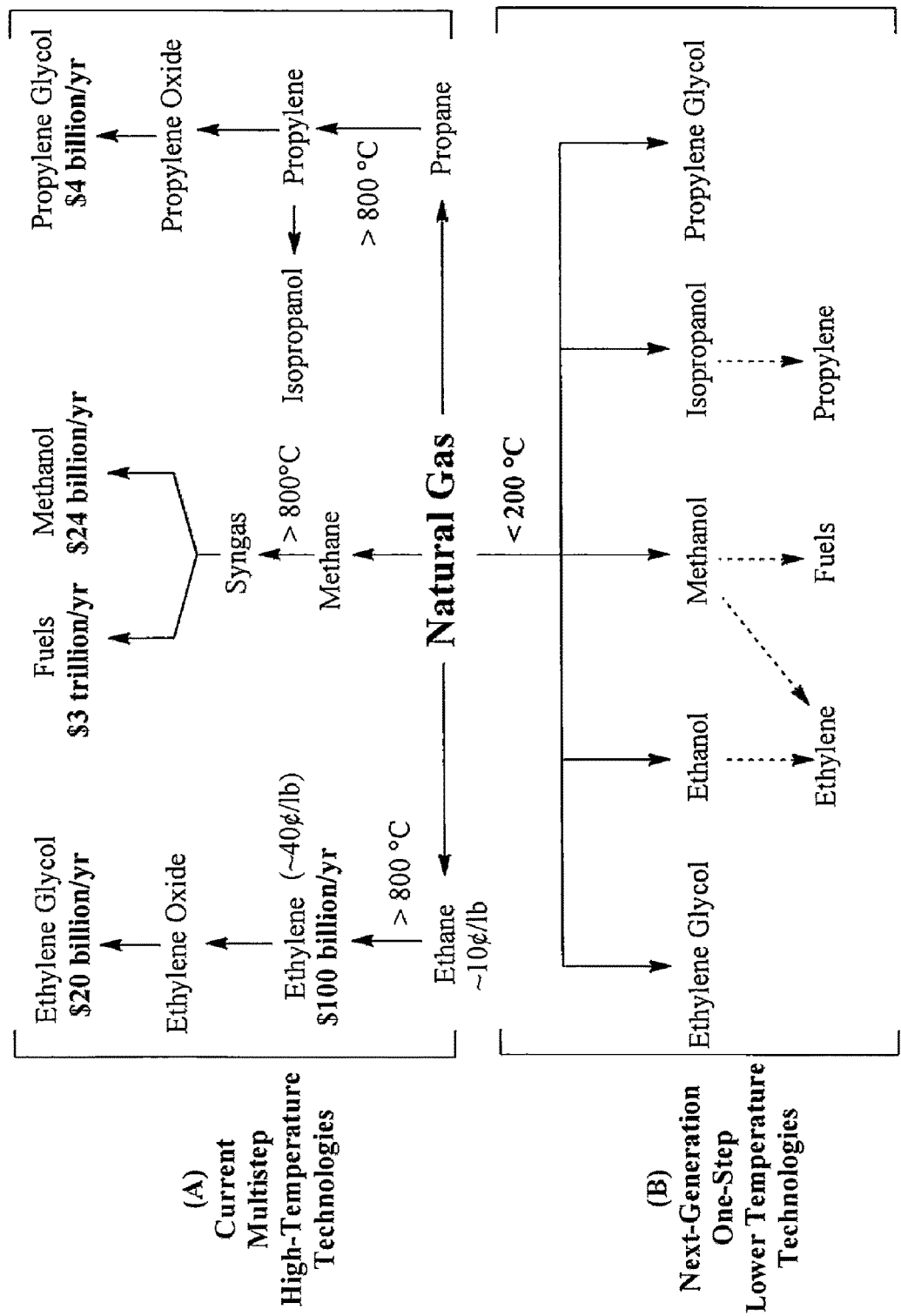
FIG. 1 is a schematic showing conversion of alkanes, such as natural gas alkanes, to functionalized alkane products: (A) lines indicate conversions accessible using prior art methods carried out at high temperatures and in multiple steps, and (B) lines indicate conversions that can be carried out using processes of the present invention at lower temperatures and in fewer steps.

The invention is directed, in various embodiments, to processes whereby alkanes, such as natural gas alkanes including methane, ethane, and propane, can be functionalized into oxygenates and other useful products under relatively mild conditions, for instance, at moderate temperatures and avoiding use of highly corrosive superacids, wherein the reagents can be recycled using inexpensive regeneration oxidants such as oxygen and hydrogen peroxide.

In prior work by one of the inventors herein, published in PCT application WO92/14738, a system was described using $Hg^{2+}$ to catalyze the reaction of concentrated (98%) sulfuric acid (i.e., a superacid) with alkanes into their corresponding alcohols and $SO_2$. The reason other more practical weaker acid solvent such as $CF_3CO_2H$ were not utilized in the above-cited work is that the key catalysts examined, $Pt^{II}$ and $Hg^{II}$, did not work in these solvents. On the basis of this we believed that the other cations, $Tl^{III}$, $Pb^{IV}$ and $Bi^V$ would also be ineffective in these weaker acids as solvents. This is important with respect to the embodiment for catalysis with those elements and with $Se^{+6}$, $Te^{+6}$, and $I^{+3}$, in $CF_3CO_2H$ and solvents of similar or lower acidity, since as we have shown that these cations do in fact react with alkanes very effectively in weaker acids such as $CF_3CO_2H$.

The present invention using soft oxidizing electrophiles as reagents in non-superacid systems represents a surprising discovery that provides alkane oxidation systems using industrially applicable materials.

A soft electrophile, as the term is used herein, relates to classification under the hard/soft acid/base (HSAB) concept, known as the Pearson acid base concept, which assigns the terms 'hard' or 'soft', and 'acid' or 'base' to chemical species. 'Hard' applies to species which are weakly polarizable, and 'soft' applies to species which are strongly polarizable. See R. G. Pearson, Chemical Hardness—Applications From Molecules to Solids, Wiley-VCH, Weinheim, 1997, 198 pp.

Table 1 is a listing of exemplary species based on Pearson hard and soft theory. Oxidizing electrophiles used in practice of methods of the present invention are classified as soft according to the HSAB theory, and include forms of main group elements such as Tl, Pb, Bi, Sb, Se, Te, and I. Higher oxidation states of these elements, as salts or compounds thereof, are used as the soft oxidizing electrophiles for practice of methods of the invention.

TABLE 1

Classification of Pearson Hard and Soft Acids

Hard Acids $H^+$, $Li^+$, $Na^+$, $K^+$, $Be^{+2}$, $Mg^{+2}$, $Ca^{+2}$, $Ba^{+2}$, $Sc^{+3}$, $La^{+2}$, $Ce^{+4}$, $Gd^{+3}$, $Lu^{+3}$, $Th^{+4}$, $U^{+4}$, $UO_2^{+2}$, $Ti^{+4}$, $Zr^{+4}$, $Hf^{+4}$, $VO^{+2}$, $Cr^{+3}$, $BF_3$, $BCl_3$, $Al^{+3}$, $AlCl_3$, $CO_2$, $RCO^+$, $NC^+$, $Si^{+4}$, $Sn^{+4}$ Borderline Acids $Fe^{+2}$, $Co^{+2}$, $Ni^{+2}$, $Zn^{+2}$, $Rh^{+3}$, $Ir^{+3}$, $Ru^{+3}$, $Os^{+3}$, $B(CH_3)_3$, $GaH_3$, $R_3C+$, $C_4H_5+$, $Sn^{+2}$, $Pb^{+2}$, $NO^+$, $Sb^{+3}$, $Bi^{+3}$, $SO_2$ Soft Acids $Pd^{+2}$, $Pt^{+2}$, $Pt^{+4}$, $Cu^+$, $Ag^+$, $Au^+$, $Cd^{+2}$, $Hg^+$, $Hg^{+2}$, $Tl^{+3}$, $Ph^{+4}$, $Bi^{+5}$, $Br^+$, $Br_2$, $I^+$, $I_2$, $Se^{+6}$, $Te^{+6}$, $I^{+3}$ Other soft acids are known to those of skill in the art, and elements having suitable pairs of oxidation states can be selected by the person of skill in the art for practicing the methods of the invention.

The present invention provides methods of alkane oxidation or functionalization that do not require the use of superacids. A superacid, as the term is used herein, refers to acids such as trifluoromethanesulfonic acid and concentrated sulfuric acid; a superacid is an acid with an acidity greater than or equal to that of concentrated sulfuric acid, which has a Hammett acidity function ($H_0$) of −12. Commercially available superacids include trifluoromethanesulfonic acid ($CF_3SO_3H$), and fluorosulfuric acid ($HSO_3F$), both of which are about a thousand times stronger (i.e. have more negative $H_0$ values) than does concentrated sulfuric acid.

Advantages of avoiding the use of superacids in the processes of the invention include lower cost, less stringent construction material demands for reactors, stability of products from higher alkanes, and ease of recycling the acidic component of the reaction milieu. Superacids can have a very high affinity for water, so any process that involves re-concentration of a superacid from water would incur prohibitively high energy costs for water removal.

The present invention thus provides improvements over the previously disclosed process employing superacids, in at least the following ways:

(a) Acid solvents weaker than 98% sulfuric acid can be used, such as trifluoroacetic acid, acetic acid, methanesulfonic acid, phosphoric acid, aqueous mineral acids or organic acids, and the like, including aqueous solutions thereof. In the previously disclosed mercury system, or the $(bpym)PtX_2$ system, very strong acids (superacids) such as 98% sulfuric acid or $CF_3SO_3H$ were required.

(b) Reactions can be carried out in the present system on a stoichiometric basis; the mercury system does not work with stoichiometric quantities of mercury or the $(bpym)PtX_2$ system.

(c) The oxidations of the present process work with methane as well as with higher alkanes. The mercury system only worked with methane, and failed with higher alkanes.

Previously, several efficient systems for the selective low temperature conversion of methane had been demonstrated based on the use of strong electrophiles such as $(bpym)Pt^{II}X_2$ and $Hg^{II}X_2$ in superacidic solvents such as $H_2SO_4$ or $CF_3SO_3H$. However, these systems are impractical on an industrial scale given the requirement for product separation by addition of water and the prohibitively expensive re-concentration to a superacidic solvent.

Efforts to develop improved systems focused on the design of catalysts that can operate in more weakly acidic media such as $CF_3CO_2H$. However, neither the $(bpym)Pt^{II}X_2$ or $Hg^{II}X_2$ systems react with alkanes in $CF_3CO_2H$ or other weakly acidic media. It is generally considered that the key reason for this failure is the reversible inhibition of the electrophilic catalyst systems with decreasing solvent acidity. This is considered to result from the increase in solvent nucleophilicity on reducing acidity that retards electrophilic CH activation through stabilization of the resting state and subsequent reduced rate of coordination of the alkane. This stabilization of the resting state and reduced rates of coordination alkane is also assumed to be the basis for reduced rates with increasing electrophilicity. This is consistent with the substantially higher reactivity of $(bpym)Pt^{II}X_2$ versus $(bpym)Pt^{IV}X_4$ for electrophilic CH activation. Consequently, given the high electrophilicity and lack of reactivity of $Hg^{II}$ with alkanes in $CF_3CO_2H$, it seemed implausible that even more powerful electrophiles such as $Tl^{III}$, $Pb^{IV}$, $Bi^V$ could react in this or other weak acid solvents.

Interestingly, studies show that the rates of water exchange with powerful electrophiles such as Hg(II) and Tl(III) can be as large as $10^{20}$ times that for electrophiles such as Ir(III), Pt(II), Pt(IV). This can be conceptually attributed to the lack of Ligand Field Stabilization Energies (LFSEs) for cations with $d^{10}$ electronic configurations such as Hg(II) and Tl(III) and high LFSE's for cations with $d^{<10}$. Counter-intuitively, these high exchange rates for strong $d^{10}$ electrophiles such as Hg(II), Tl(III), Pb(IV) and Bi(V) could suggest that the expected correlation between increasing electrophilicity and reduced rates of CH activation may be incorrect. Indeed, our studies now show that increasing electrophilicity actually increase the rate of CH activation in the $d^{10}$ cations with Pb(IV)>Tl(III)>>Hg(II). This is interesting since it suggest that $Hg^{II}$ does not react in $CF_3CO_2H$ because the electrophilicity is too low rather than too high. This is a very important observation since it suggests that other inexpensive, abundant post transition metal cations could be designed for the activation and functionalization of alkanes in non-superacidic media. Given the low toxicity and common use of bismuth, iodine, antimony, etc., the design of homogeneous system based on these cations is particularly attractive.

A main group element, as the term is used herein, refers to metals and non-metals, including elements of CAS groups IIIA, IVA, VA, VIA, and VIIA, that are post-transition elements, i.e., being of higher atomic number than the last element of the first transition series, Zn, i.e., of atomic number>30. Thus, a soft oxidizing electrophile used in practice of methods of the invention includes elements having stable isotopic forms of atomic numbers 31-35, 49-53, and 81-83. The element, in some embodiments, has a $d^{10}$ electronic configuration. However, a soft oxidizing electrophile used in practice of a method of the invention can have other than a $d^{10}$ electronic configuration.

Figure 5:
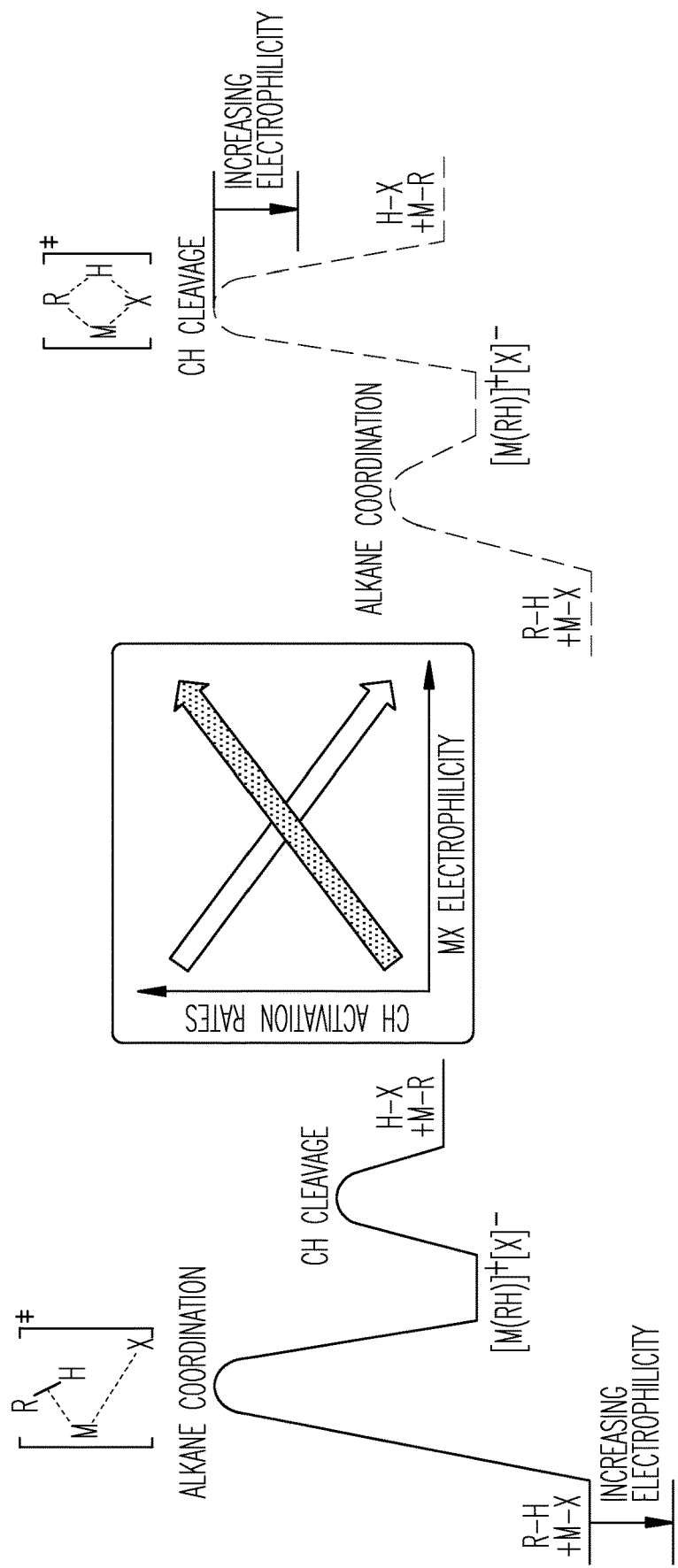
FIG. 5 depicts conceptual energy diagrams illustrating the relative rates of the two key steps in the overall CH activation of alkanes (R—H) by M-X metal complexes. The rate-limiting step in the solid line, left-hand diagram is alkane coordination. In this case, the resting state is net stabilized by increasing the electrophilicity of M-X. In the dashed line, right-hand diagram the rate-limiting step is CH bond cleavage. In this case, the transition state for C—H cleavage is net stabilized by increasing the M-X electrophilicity. The predicted trends in overall rate of CH activation with increasing electrophilicity of M-X for these cases are shown in the inset. The plain arrow is associated with the left-hand, solid line diagram and the dotted arrow is associated with the dashed line, right-hand diagram.

Studies initially suggested that both the original Hg and $(bpym)PtX_2$ systems operated by electrophilic CH activation, and that the lack of reaction in weaker non-superacid solvents resulted from effectively complete inhibition of this step in these media.[30] As shown conceptually in FIG. 5, electrophilic CH activation by M-X transition metal complexes are typically considered to proceed through two general steps involving i) alkane R—H coordination to M-X to generate $[M(R-H)]^+ + X^-$ followed by ii) CH bond cleavage to generate M-R. Studies show that CH activation by the (bpym)Pt system operate by the solid line, left-hand diagram in FIG. 5 where R—H coordination is rate limiting, and inhibition in moving from superacid to weaker acid solvents result from stronger coordination of the more nucleophilic anions, $X^-$, present in weaker acid solvents to the electrophilic metal center. This results in net stabilization of the M-X resting state and increases the barrier to R—H coordination and CH activation.

Interestingly, at the time of these discoveries we, in retrospect, erroneously considered that all electrophilic CH activation systems would operate by the model shown in solid line, left-hand portion of FIG. 5. Consequently, we assumed that stabilization of the resting state also accounted for the inhibition of $Hg^{II}$ in weaker, non-superacid media as well as the counterintuitive observations in both the (bypm) Pt and Shilov PtCl systems that the higher oxidation state $Pt^{IV}$ is effectively inactive whereas lower oxidations state $Pt^{II}$ exhibits high rates of electrophilic CH activation. Importantly, for systems operating by the solid line, left-hand energy diagram in FIG. 5, it could be expected that the relative rate of CH activation would decrease with increasing electrophilicity (FIG. 5, inset graph, clear arrow). Between this resting state stabilization model and concerns of possible radical reactions, our studies were directed away from $Tl^{III}$, $Pb^{IV}$ and other main group cations that were more strongly oxidizing and electrophilic than $Pt^{II}$ ($E°$=~0.8 V)[29] and $Hg^{II}$ for functionalization of higher alkanes in non-superacid media.

Thus, it was surprising that we would discover alkane functionalization systems in which superacids, the presence of which had been found to be required in prior art alkane oxidation systems involving C—H bond insertion of main group or transition elements, are not required.

Contrary to the predictions discussed above, we have surprisingly discovered that soft oxidizing electrophiles $Tl^{III}(TFA)_3$ and $Pb^{IV}(TFA)_4$, among others, can rapidly functionalize methane, ethane and propane separately or as mixtures, in high selectivity and concentrations, to the corresponding trifluoroacetate esters of methanol (MeTFA), ethanol (EtTFA), ethylene glycol (EG(TFA)$_2$), isopropanol (iPrTFA), and 1,2-propylene glycol (PG(TFA)$_2$) (Table 2: entries 1-6, 8, 9, 12-15). Table 2 shows data relating to the reaction of lead and thallium based soft oxidizing electrophiles with methane, ethane, and/or propane.

d-orbitals and strong LFSE for cations with unfilled d-orbitals. On the basis of these enormous differences in exchange rates it is plausible that the rate of alkane coordination for main group $d^{10}$ electrophiles could be fast and CH bond cleavage comparatively slow and rate limiting (FIG. 5, dashed line, right-hand lines) for the overall CH activation process. It is also plausible that with this switch in the rate-limiting step that increasing electrophilicity could result in a net lowering of the transition state for CH bond cleavage. This can be explained by Hard Soft Acid Base (HSAB) theory whereby an increase in the M-C bond strength would be expected with increasing electrophilicity of these soft, polarizable, third-row, $d^{10}$ electrophiles.[32] As shown in FIG. 5, these considerations lead to the prediction that the rate of electrophilic CH activation, (FIG. 5, inset graph, dotted arrow) with these main group, $d^{10}$ cations

TABLE 2

Reaction of Tl and Pb Oxidants with Methane, Ethane, and/or Propane.

| Entry | Oxidant | Conc (M) | Solvent | Hydrocarbon | Products (% of Total Products) | Yield ([Product]) |
|---|---|---|---|---|---|---|
| 1 | Tl(TFA)$_3$ | 0.250 | HTFA | MeH | MeTFA (100%) | 74% (0.19M) |
| 2* | Tl(TFA)$_3$ | 2 | HTFA | MeH | MeTFA (100%) | 55% (1.1M) |
| 3 | Tl(TFA)$_3$ | 0.250 | HTFA | EtH | EtTFA (67%), EG(TFA)$_2$ (33%) | 75% (0.16M) |
| 4 | Tl(TFA)$_3$ | 3 | HTFA | EtH | EtTFA (64%), EG(TFA)$_2$ (36%) | 60% (1.48M) |
| 5 | Tl(TFA)$_3$ | 0.250 | HTFA | PrH | iPrTFA (77%), PG(TFA)$_2$ (23%) | >95% (>0.22M) |
| 6 | Tl(TFA)$_3$ | 0.250 | HTFA | 100(MeH):8(EtH):1(PrH) † | MeTFA (9%), EtTFA (21%), EG(TFA)$_2$ (11%), iPrTFA (10%), PG(TFA)$_2$ (19%) | 82% (0.11M) |
| 7‡ | Tl(TFA)$_3$ | 0.250 | HTFA/H$_2$O | EtH | EtTFA (68%), EG(TFA)$_2$ (32%) | 73% (0.16M) |
| 8§ | Tl(TFA)$_3$ | 0.250 | HTFA | EtH | EtTFA (66%), EG(TFA)$_2$ (34%) | 76% (0.16M) |
| 9‖ | Tl(TFA)$_3$ | 0.250 | HTFA | EtH | EtTFA (65%), EG(TFA)$_2$ (35%) | 30% (0.06M) |
| 10 | Tl(TFA)$_3$ | 0.250 | MSA | EtH | EtX (47%), EG(X)$_2$ (53%)¶ | 93% (0.18M) |
| 11 | Tl(OAc)$_3$ | 0.250 | HOAc | EtH | EtOAc (2%), EG(OAc)$_2$ (98%) | 43% (0.06M) |
| 12 | Pb(TFA)$_4$ | 0.250 | HTFA | MeH | MeTFA (100%) | 76% (0.19M) |
| 13 | Pb(TFA)$_4$ | 0.250 | HTFA | EtH | EtTFA (70%), EG(TFA)$_2$ (30%) | 90% (0.2M) |
| 14‖ | Pb(TFA)$_4$ | 0.250 | HTFA | EtH | EtTFA (68%), EG(TFA$_2$ (32%) | 75% (0.18M) |
| 15 | Hg(TFA)$_2$ | 0.250 | HTFA | EtH | N/A | 0% (0.0M) |

Standard Conditions: 0.25M Tl(TFA)$_3$ or Pb(TFA)$_4$ in 2 ml TFAH, gas pressure (MeH = 500 psig, EtH = 500 psig, or PrH = 125 psig), 180° C. for 3 h. Conc (M) = (mol oxidant)/(L solvent added). Product Selectivity = [Individual Liquid Product]/[Total Liquid Products] × 100. Yield based on $^1$H-NMR = [Oxidant]/[Total Liquid Products] × 100, [Product] = (mol Product)/(L solvent added).
*Pressure = 800 psig and T = 190° C.
† Total pressure = 500 psig.
‡Run with 2M H$_2$O present.
§Run with 15 psi O$_2$ present.
‖Reactions were run at 150° C.
¶Products were a mixture of EtTFA, Et(MSA), EG(TFA)$_2$, and EG(MSA)$_2$.

We focused primarily on trifluoroacetic acid (HTFA) as the reaction medium, but also observed efficient reactivity in other non-superacidic solvents such as methane sulfonic acid (MSA, entry 10), (HOAc, entry 11), and TFAH/H$_2$O mixtures (entry 7). Importantly, in contrast to the reported reactions with (bpym)Pt$^{II}$ or Hg$^{II}$ in superacid media, no evidence for C—C cleavage or other side products were observed with the higher alkanes, ethane and propane.

In spite of the original concerns of radical reactions and inhibition of CH activation in non-super acid media, we nonetheless believe it is plausible to rationalize the reactions of these non-transition metal, main group, $d^{10}$ cations with alkanes by a general reaction mechanism involving electrophilic CH activation and M-R functionalization that have primarily been associated with transition metals.

Some of the earliest studies on ligand interaction with metal cations show that the rates of ligand exchange for the third row, main group, $d^{10}$, strong electrophiles such as Hg$^{II}$ and Tl$^{III}$ are ~$10^{19}$ faster than for the transition metal, $d^{<10}$, cations such as Ir$^{III}$ or Pt$^{IV}$.[31] These extraordinary differences in rate are conceptually attributed to lack of Ligand Field Stabilization Energies (LFSE) for cations with filled could increase with increasing electrophilicity (assuming that alkane coordination continues to be fast). Significantly, this is opposite to the trend in our earlier model (FIG. 5, inset graph, clear arrow). Counter-intuitively, this new model suggests that the lack of reaction of Hg$^{II}$ in weaker acid media was because its electrophilicity was too low rather than too high. These considerations led us to more closely examine the reaction mechanism of the Tl$^{III}$-mediated alkane oxidation.

Figure 6:
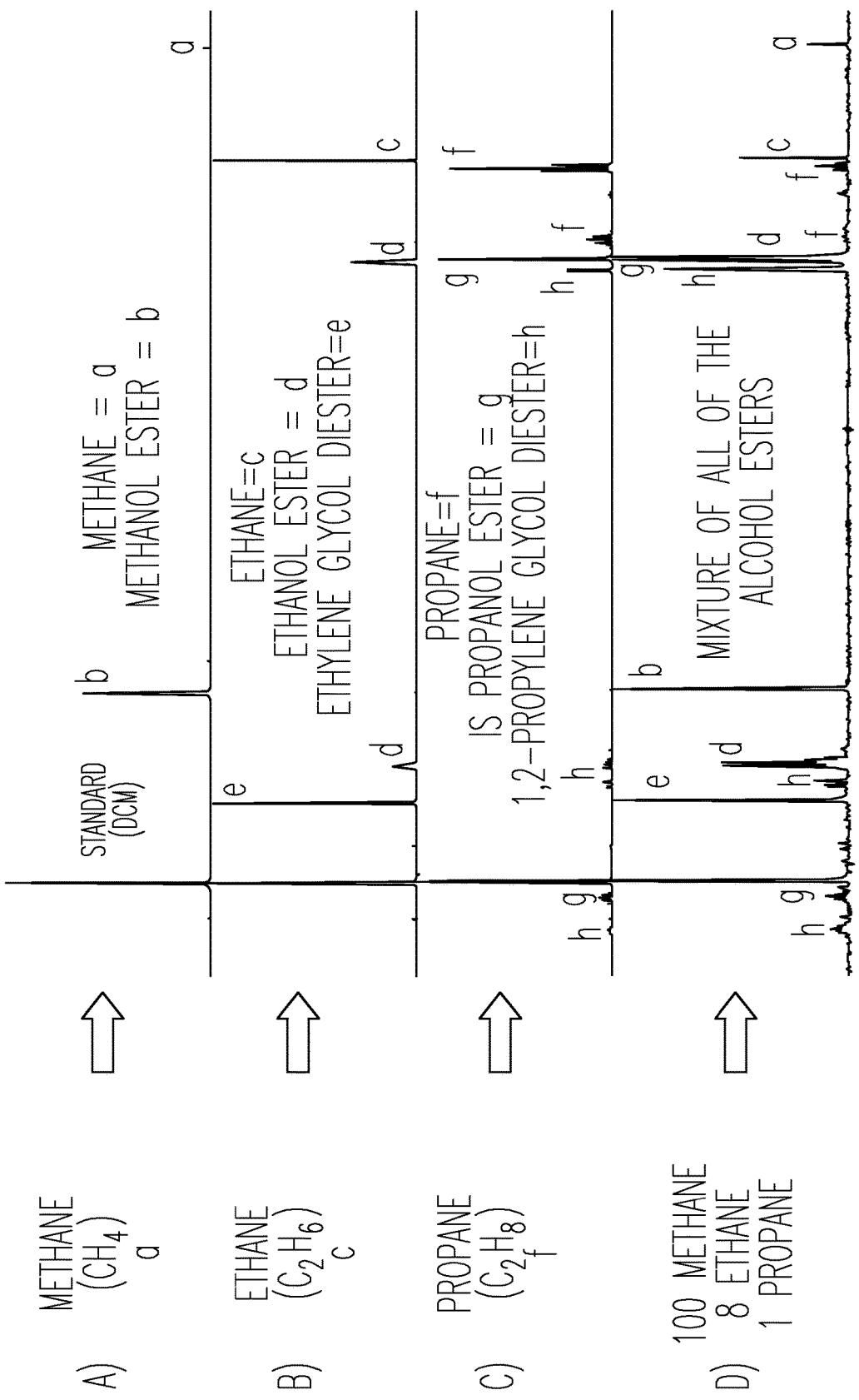
FIG. 6 shows stacked $^1$H-NMR (400 MHz) spectra of the crude reaction mixtures in TFAH after Tl(III)-mediated oxidation of: A) methane, B) ethane, C) propane, and D) a mixture of methane, ethane and propane in ratio typical in natural gas. The products are the alcohol esters of trifluoroacetic acid.

The crude mixtures from the reactions of Tl$^{III}$ with the alkane in TFAH are homogeneous and effectively colorless. The $^1$H-NMR spectra of the crude reaction mixtures in TFAH from separate reactions of 500 psig of methane and ethane, and 125 psig of propane with Tl(TFA)$_3$ in CF$_3$CO$_2$H solvent at 180° C. for 3 h, are shown in FIG. 6 A-C. A coaxial insert was utilized as an external standard. The TFA-ester of methanol (MeTFA), and the corresponding esters of ethanol (EtTFA) and ethylene glycol (EG(TFA)$_2$) are the only products observed (within a 1% detection threshold) from methane and ethane, respectively.

Remarkably, the reaction with propane (Table 2: entry 5) is also very efficient and only generates the corresponding esters of isopropanol (iPrTFA) and 1,2-propylene glycol (PG(TFA)$_2$). Reactions conducted with 100% $^{13}$C-labeled methane ($^{13}$CH$_4$) and ethane ($^{13}$C$_2$H$_6$) unambiguously confirmed that the esters are formed from the corresponding alkanes. Exclusively $^{13}$C-labeled products were observed in the liquid phase and only traces of $^{13}$CO$_2$ were detected in the gas phase. No products from C—C cleavage or other side reactions were observed in the liquid phases. Consistent with this high selectivity, control studies showed that the ester products are unreactive toward Tl(TFA)$_3$ when the hydrocarbon gas is replaced with argon under otherwise identical conditions. Assuming a detection limit of 1% and a 5 mM methane concentration in the liquid phase, the parent alkanes appear to be at least 100 times more reactive than the alcohol ester products.

R—H+Tl(TFA)$_3$→Tl(TFA)+TFAH+R-TFA   (eq. 2)

Consistent with the 1:1 metal:alkane stoichiometry shown in eq. 2, analysis of a crude reaction mixture with ethane by Tl-NMR before and after a reaction shows unreacted Tl$^{III}$ as well as Tl$^I$. To examine whether alkanes such as methane, ethane, and propane could be functionalized without separation in a one-pot procedure, we prepared and examined the reaction of a mixture of methane, ethane, and propane in a 100:8:1 ratio typical in natural gas. As can be seen from $^1$H and $^{13}$C-NMR analysis of the crude reaction mixture in TFAH, FIG. 6D, each alkane is converted to the corresponding alcohol esters, in high selectivity in a molar ratio of MeTFA:(EtTFA+EG(TFA)$_2$):(iPrTFA+PG(TFA)$_2$) of ~1:3:3. When normalized for the number of hydrogens in each of the alkanes, the relative reactivity of the CH bonds in methane, ethane, and propane is ~1:25:150. This trend is also consistent with an electrophilic reaction that would be expected to proceed faster with the higher, more electron rich alkanes.

As discussed above, a prediction of the dashed line, right-hand reaction model in FIG. 5 is that in contrast to our earlier model for electrophilic CH activation the rates of alkane functionalization should increase with increasing electrophilicity. Indeed, under identical conditions, in the absence of mass transfer limitations and at shorter reaction times to minimize conversion of the salts, the total yield of EtTFA and EG(TFA)$_2$ from Hg$^{II}$(TFA)$_2$, Tl$^{III}$(TFA)$_3$, and Pb$^{IV}$(TFA)$_4$ was 0%, 30%, and 75%, respectively (Table 2, Entries 15, 9, and 14).

Our results qualitatively show that the relative rates of reactivity of these electrophiles with ethane in TFAH is Hg$^{II}$ (inactive)<<Tl$^{III}$<Pb$^{IV}$. If the trend holds through this third row, d$^{10}$ series it is possible that Bi$^V$ could be very reactive with alkanes. Bi$^V$(TFA)$_5$ is unknown and efforts are underway to synthesize and study this species.

These observations support a proposed electrophilic CH activation/M-R functionalization mechanism. However, given the general consideration that strongly oxidizing species can generate free radical reactions with alkanes we were prompted to carry out further mechanistic studies. Varying the alkane pressure shows a first-order rate dependence (k$_{obs}$=1.8×10$^{-8}$±8.9×10$^{-10}$ s$^{-1}$·psi$^{-1}$) on alkane. Some key characteristics of free-radical reactions can be, but not always, poor reproducibility and changes in reaction rate and product selectivity in the presence of radical traps, such as O$_2$.$^{28}$ To examine these possibilities, we studied the kinetics for the reaction of Tl(TFA)$_3$ with a 33-fold excess of ethane in TFAH. The reaction exhibits highly reproducible, clean first-order (in Tl$^{III}$) kinetics (k$_{obs}$=6.2×10$^{-7}$±3.1×10$^{-8}$ s$^{-1}$·psi$^{-1}$) for the generation of the TFA esters of EtTFA and EG(TFA)$_2$ with no induction period. Interestingly, analysis of the relative rates of formation of EtTFA and EG(TFA)$_2$ is consistent with parallel, rather than the expected sequential, formation of these products. These results would suggest a common intermediate, plausibly a Tl$^{III}$-Et species, for the formation of both products (see FIG. 7). Carrying out the reaction in the presence of added O$_2$ (a well-known radical trap that is stable under these reaction conditions) had no effect on the reaction rate or selectivity (Table 2, Entry 8). As noted above, these results along with the high reaction selectivity and lack of any C—C cleavage products in the reaction of ethane and propane with Tl(TFA)$_3$ strongly argue against a free radical mechanism.

To further investigate the possibility of a CH activation/ M-R functionalization mechanism, we carried out the reaction of methane with Tl(TFA)$_3$ in deuterated trifluoroacetic acid, DTFA. Only CH$_3$TFA was generated in this reaction, and no CH$_3$D was observed. This result would be consistent with a reaction mechanism where CH activation step is rate limiting and irreversible whereas functionalization of the putative Tl$^{III}$—CH$_3$ intermediate to the alcohol ester is fast. Consistent with assignment of CH bond cleavage as the rate-limiting step, the intramolecular kinetic isotope effect (KIE) based on reactions with H$_3$C—CD$_3$ was measured to be 3.4. A very small KIE or no KIE would be expected if alkane coordination or M-R functionalization were rate limiting. The expected putative (TFA)$_2$Tl$^{III}$-Me intermediate is unknown and likely unstable.

However, the dimethyl species, (TFA)Tl(CH$_3$)$_2$ is stable in TFAH at room temperature. Because this class of organometallic is well known to undergo rapid alkyl transfer, we examined the reaction of (TFA)Tl(CH$_3$)$_2$ with Tl(TFA)$_3$ as a means of generating (TFA)$_2$Tl$^{III}$-Me in situ. Upon addition of Tl(TFA)$_3$ at room temperature to a solution of (TFA)Tl(CH$_3$)$_2$ in TFAH, within minutes two equivalents of MeTFA were cleanly generated in quantitative yield relative to (TFA)Tl(CH$_3$)$_2$ based on the stoichiometry shown in eq. 3. Analysis of the crude reaction mixture by NMR immediately upon mixing showed a new, broad, transient Me-species that could be the (TFA)$_2$Tl(CH$_3$) intermediate. Consistent with the lack of H/D exchange in reactions of CH$_4$ with Tl(TFA)$_3$ in DTFA (which we attributed to irreversible formation of the putative (TFA)$_2$Tl$^{III}$-Me intermediate), no CH$_4$ is generated from these functionalization reactions of (TFA)Tl(CH$_3$)$_2$ with Tl(TFA)$_3$ in TFAH. These results are also consistent with reports that treatment of (OAc)$_2$TlMe with HOAc generates MeOAc.$^{33}$

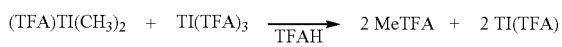

(eq. 3)

(TFA)Tl(CH$_3$)$_2$ + Tl(TFA)$_3$ →[TFAH] 2 MeTFA + 2 Tl(TFA)

Figure 7A:
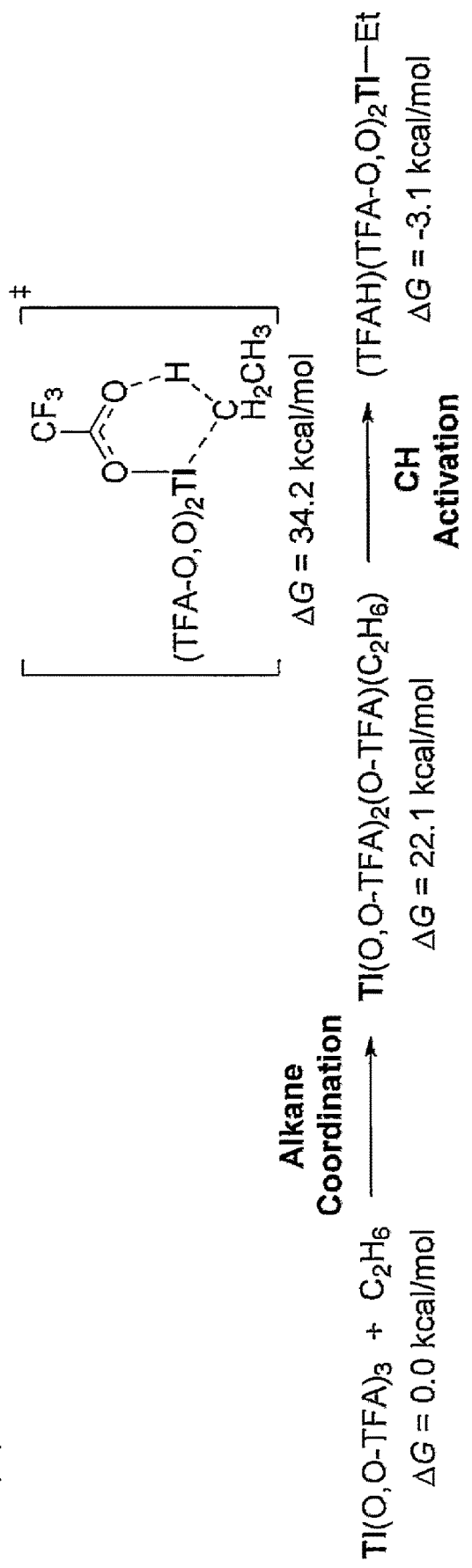
FIG. 7 shows M06/6-31+G(d,p)[LANL2DZ] DFT calculated (A) Tl(III) CH activation and (B) Tl-Et functionalization pathways in trifluoroacetic acid (TFAH) solvent.

We have also used M06 density functional theory calculations to examine possible mechanisms and the energy landscape for ethane CH functionalization, as well as to postulate a mechanism that accounts for the parallel formation of EtTFA and EG(TFA)$_2$. To begin, we examined whether it is plausible that Tl(TFA)$_3$ could induce functionalization of ethane by a radical or one electron oxidation pathway. Radical chain mechanisms beginning with a reactive (TFA)$_2$Tl./CF$_3$COO. radical pair were ruled out because Tl—O bond homolysis requires 52.3 kcal/mol of free energy. Additionally, one electron oxidation and Tl mediated hydrogen atom abstraction were also ruled out because these pathways require greater than 75 kcal/mol. Instead, our calculations suggest the most viable pathway for CH functionalization is CH activation by electrophilic substitution (FIG. 7A). Calculations show that the ground state for Tl(TFA)$_3$ is with both oxygen atoms of the three TFA anions coordinated to the Tl center in an octahedral geometry, Tl(O,O-TFA)$_3$.

Figure 7B:
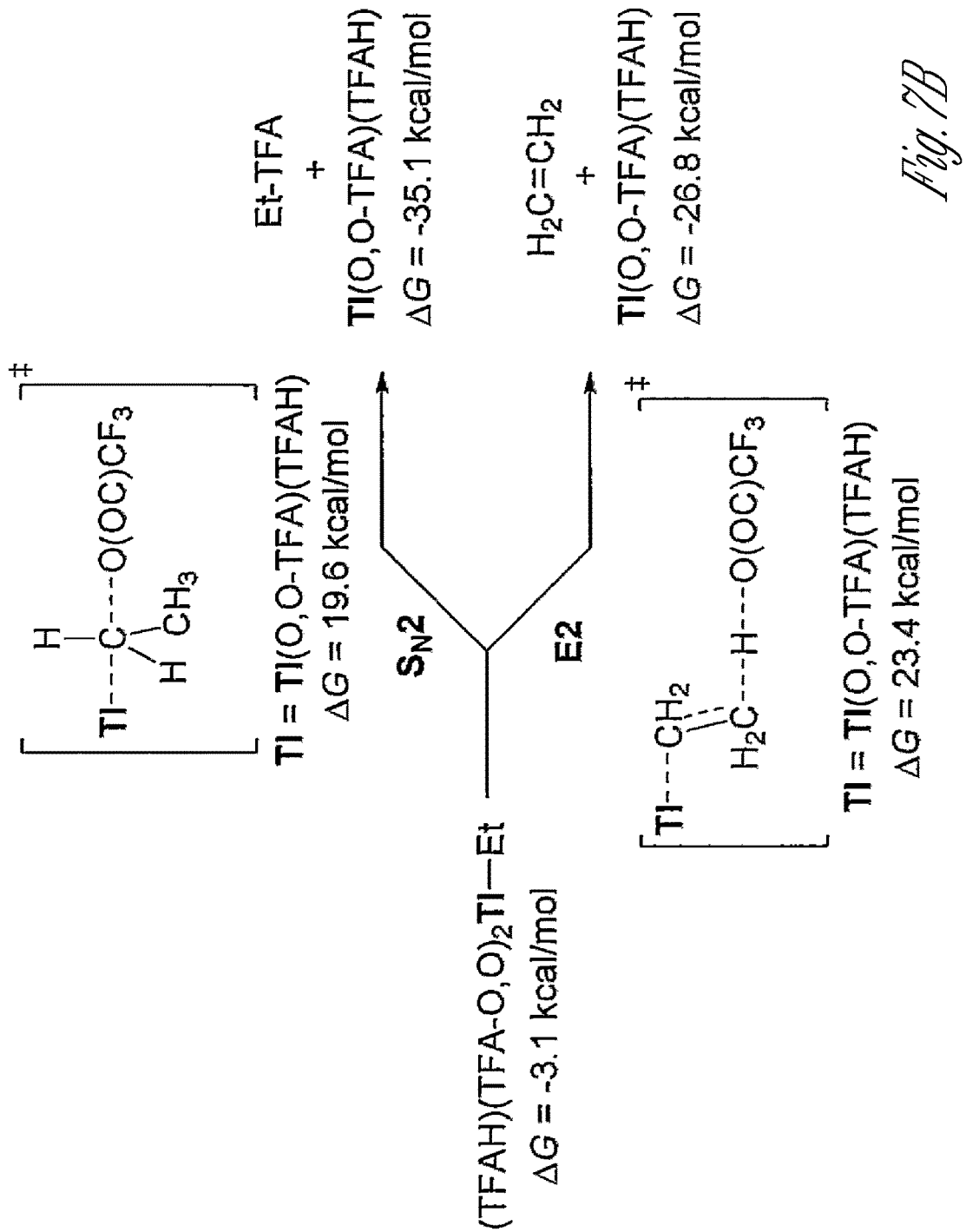

Examination of the structure shows that one oxygen atom in each coordinated TFA is more tightly bound than the other. The calculations show that ethane coordination occurs by dissociation of one oxygen in a 0,0-TFA anion to generate an open coordination site that allows for ethane coordination to give (O,O-TFA)$_2$(O-TFA)Tl(C$_2$H$_6$). As anticipated on the basis of the conceptual model shown in FIG. 5 (dashed line, right-hand energy diagram), the d$^{10}$ main group metal centers exhibit rapid coordination of an alkane and this requires only $\Delta G=22.1$ kcal/mol. This value contrasts with the >35 kcal/mol for alkane coordination in the (bpym)Pt$^{II}$ system in superacid media. Subsequent CH bond cleavage from (O,O-TFA)$_2$(O-TFA)Tl(C$_2$H$_6$) by an electrophilic substitution transition state at $\Delta G^{\ddagger}=34.2$ kcal/mol is consistent with the rates of reactions observed and with rate-limiting CH bond cleavage (FIG. 7B). Consistent with the experimentally measured KIE of 3.4, in this CH bond cleavage transition state there is considerable Tl—C bond formation and C—H bond stretching. Calculation of the KIE based on this transition state gave a value of 4.7.

The thermodynamics for the CH activation step suggests that the Tl-Et species is slightly more stable than the Tl(TFA)$_3$ salt and ethane ($\Delta G=-3.1$ kcal/mol). Thus a Tl-Et species might be observable. However, calculations predict that Tl-Et functionalization has a much lower barrier than CH activation and therefore functionalization of the Tl-Et species is much more rapid than the CH activation reaction. This explains the lack of H/D exchange when the reactions are run in deuterated TFAD as well as the quantitative yield of MeTFA without any CH$_4$ formation from the reaction of (TFA)TlMe$_2$ with Tl(TFA)$_3$ to TFAH. FIG. 7B shows the two most plausible pathways for functionalization of Tl-Et identified by calculations. The S$_N$2 pathway forms Et-TFA whereas the E2 pathway forms ethylene. Control experiments show that although conversion of Et-TFA to EG(TFA)$_2$ is slow, ethylene in rapidly converted to EG(TFA)$_2$ by reaction with Tl(TFA)$_2$. The calculations suggest that although the S$_N$2 and E2 pathways are competitive, there is a preference for the S$_N$2 pathway. This is consistent with experiment showing parallel but higher rates of formation of Et-TFA relative to EG(TFA)$_2$. Additionally, our calculations also show that the $\Delta G^1$ for CH activation of the methyl group of Et-TFA is greater than 40 kcal/mol because the TFA group imparts a strong electron-withdrawing influence even two carbons away. This result is consistent with the high reaction selectivity and suggests that EG(TFA)$_2$ is formed from the E2 functionalization pathway rather than functionalization of Et-TFA.

Experiment and theory taken together strongly support the proposed mechanism for alkane functionalization involving slow, irreversible electrophilic activation of alkanes with third-row, main group cations, M$^n$X$_n$ to generate M$^n$-R intermediates followed by fast M-R functionalization to generate RX and M$^{n-2}$X$_{n-2}$. Applying this new understanding to reactions of other main group, d$^{10}$ cations, M$^n$X$_n$, with alkanes, either in two separate stoichiometric reactions or with M$^n$X$_n$ as a catalyst, the inventors herein have devised practical processes for the selective hydroxylation of alkanes to alcohols using air or other oxidants such as H$_2$O$_2$.

This invention provides, in various embodiments, processes encompassing the use of novel reagents that facilitate the conversion of alkanes directly, selectively and in high yields and volumetric productivity to the corresponding alcohols at temperatures below 300° C., such as in liquid phase batch reactors. The overall reaction is the partial oxidation of the alkanes with oxygen or air to the corresponding alcohols. The alcohols can then be used as chemicals or fuels or can be converted to other materials. The reagents can be regenerated to active form by the use of an oxidizer, such as H$_2$O$_2$, atmospheric oxygen, nitric acid, halogens, and the like. It is within ordinary skill for the practitioner to select the oxidizer suitable for the specific M$^n$X$_n$ reagent used in the alkane functionalization reaction. Key advantages to these reactions include avoiding the high temperature, multistep, complex and capital intensive processes that are currently use for the conversion of alkanes to functional products such as olefins, diesel or methanol. Examples of these advantages are illustrated in the scheme shown in FIG. 1. As shown in FIG. 1(B), the invention described in this disclosure would allow new, more direct processes for the conversion of the alkanes to alcohol products when compared to the existing processes, FIG. 1(A). Capital and operating costs are in many cases the major contribution to the production costs for these large volume materials. Reducing the number of steps, temperatures, heat management and reactor cost would substantially reduce these costs as well as overall energy while increasing atom efficiencies for the generation of the species from alkane-rich feedstocks such as natural gas.

An outstanding feature of various embodiments of the soft oxidizing electrophiles useful in carrying out the methods of the present invention are that they are based on inexpensive main group elements, such as thallium, lead, bismuth, antimony, selenium, iodine, and the like, and can convert each alkane to a corresponding functionalized alkane separately or as part of a mixture. Significantly, these direct conversions avoid the high temperature and resulting large capital investment required by current indirect processes that proceed by generation of syngas or olefinic intermediates. The discovery of these catalyst/reagent designs build on new alkane CH activation chemistry developed over the last 20 years that enables the cleavage of CH bond without the generation of the free radicals involved in oxidation technologies presently used in the industry. It is projected that these novel catalyst designs will be the basis for proprietary platform technologies resulting in the lowest cost commercial processes for the conversion of natural gas to chemicals, liquid fuels and lubricants. This will make possible monetization of associated and stranded gas as well as substantially increasing the market and value for the extensive natural gas reserves throughout the US and the world. The technology as disclosed and claimed in the present patent application could allow natural gas to be used to augment and potentially displace the use of petroleum.

The present invention provides, in various embodiments, a process for the oxidation of an alkane to an alkane oxygenate, comprising (a) contacting the alkane and a soft oxidizing electrophile comprising a main group element in oxidized form, or contacting the alkane and a reduced form of the soft oxidizing electrophile plus an oxidant, in an acidic medium comprising an oxygen acid, in the absence of a super-acid, at a temperature of less than 300° C., to provide the alkane oxygenate and an electrophile reduction product; and (b) separating the alkane oxygenate and the electrophile reduction product.

As disclosed herein, the soft oxidizing electrophile and the acidic medium can be selected by the skilled practitioner from a variety of options, disclosed and claimed herein. The soft oxidizing electrophile and the electrophile reduction product, as well as the reduced form of the soft oxidizing electrophile, are discussed throughout the present application. The acidic medium comprises an oxygen acid, by which is meant an acid wherein the acidic proton is bonded to an oxygen atom, e.g., trifluoroacetic acid acetic acid, methanesulfonic acid, and the like. The reaction does not require the presence of a superacid, and can be carried out at attractively low temperatures and pressures. In the examples shown in Table 2, above, high conversion were achieved at pressures of about 500 psig for methane and ethane and at temperatures of about 150° C.

The process of the invention can further comprise (c) contacting the separated electrophile reduction product and an oxidizing regeneration reagent, to regenerate the soft oxidizing electrophile.

Figure 2:
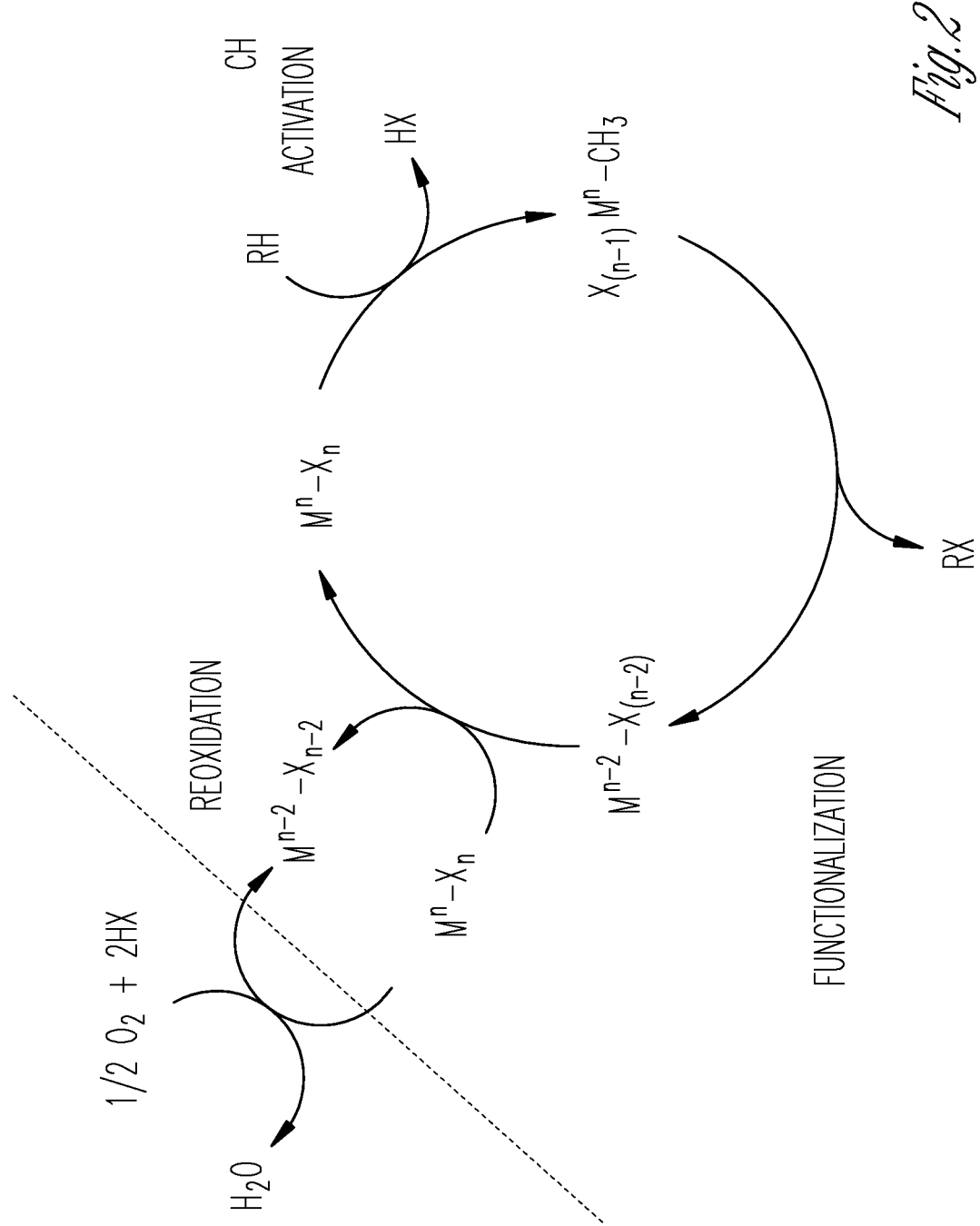
FIG. 2 is a reaction scheme showing a proposed cycle of reactions whereby a process of the invention can be used to accomplish an overall conversion of an alkane to a functionalized alkane such as a corresponding alcohol.

By this recycling step, a large proportion of the main group element of the soft oxidizing electrophile can be captured and reused, providing economic and environmental advantages. See FIG. 2. By an oxidizing regeneration reagent is meant an oxidizing molecular entity such as hydrogen peroxide, oxygen, nitric acid, a halogen, and the like. The skilled practitioner can, based on knowledge of electrochemical potentials and the like select the suitable oxidizing regeneration reagent for the particular $M^nX_n$ reduction product of the specific system being used. The regeneration of the alkane-reactive soft oxidizing electrophile can be carried out in situ, where the soft oxidizing electrophile functions as a catalyst; or can be carried in alternating cycles where the soft oxidizing electrophile serves as a stoichiometric oxidant of the alkane and is regenerated in a separate step.

In various embodiments, a stoichiometric or greater quantity of the soft oxidizing electrophile relative to the hydrocarbon can be present, and the M-R activated intermediate can be formed in a single step, e.g., without regeneration of the $MX_n$ soft oxidizing electrophile in situ.

Alternatively, the oxidizing regeneration reagent can be an oxidizing electrochemical potential, i.e., where a sufficient voltage is applied to form or regenerate the soft oxidizing electrophile from the electrophile reduction product.

For example, the soft oxidizing electrophile can comprise the element thallium, lead, bismuth, selenium, tellurium, or iodine, in oxidized form. For instance, the soft oxidizing electrophile can comprise Tl(III), Pb(IV), Bi(V), Se(VI), Te(VI), I(III), or I(V). By this nomenclature, the oxidation state of the element is referred to, e.g., Tl(III), also written as $Tl^{III}$, being $Tl^{+3}$, and the same for the other elements described. The soft oxidizing electrophile can be a molecular species of formula $M^nX_n$, wherein M is a metal or non-metal cation of a main group element of atomic number 31-35, 49-53, and 81-83, in an oxidation state of n, X is an anionic counterion. The counterion can be a conjugate base of an acid, e.g., $CF_3CO_2^-$, $HOSO_2O^-$, $CH_3SO_2O^-$, or $CH_3CO_2^-$. The integer "n" is the number of anions needed to balance the metal positive charge, which can also be equal to n. In various embodiments, the soft oxidizing electrophile comprising a main group element in oxidized form is a salt wherein the counterion of the main group element in oxidized form is a conjugate anion of an acid of the acidic medium. When the soft oxidizing electrophile is referred to as a salt, it is understood that there may be a significant degree of covalent character to the compound formed by the main group element in oxidized form and the anionic counterion.

For instance, in embodiments wherein the acidic medium comprises trifluoroacetic acid, acetic acid, methanesulfonic acid, phosphoric acids, phosphonic acids, aqueous mineral acids, aqueous organic acids and the like; and the counterion of main group element in oxidized form is trifluoroacetate, acetate, methanesulfonate, phosphate, etc., respectively.

For a soft oxidizing electrophile of formula $M^nX_n$, M is a metal or non-metal cation of a main group element of atomic number 31-35, 49-53, and 81-83, in an oxidation state of +n, and X is a counterion, such as a trifluoroacetate, etc. For instance, the counterion can be the conjugate base of the oxygen acid of the acidic reaction medium. With the M element in oxidation state +n, the electrophile reduction product can be in an oxidation state of +(n−2) or +(n−1); that is, the insertion into the C—H bond of the alkane can be accompanied by a two electron reduction or a one electron reduction of the main group element, respectively. It is apparent that the overall stoichiometry of the C—H insertion reaction will vary accordingly.

In various embodiments, a process of the invention comprises contacting the alkane and a soft oxidizing electrophile comprising a main group element in oxidized form, in an acidic medium comprising an oxygen acid, in the absence of a super-acid, at a temperature of less than 300° C., to provide the alkane oxygenate and an electrophile reduction product. With the soft oxidizing electrophile in oxidized form, reaction with the alkane proceeds directly, in the absence of a superacid, and at a temperature of less than 300° C., preferably less than 200° C. In various other embodiments, a process of the invention comprises contacting the alkane and a reduced form of the soft oxidizing electrophile plus an oxidant, in an acidic medium comprising an oxygen acid, in the absence of a super-acid, at a temperature of less than 300° C., to provide the alkane oxygenate and an electrophile reduction product. In such embodiments, the oxidized form is generated in situ by reaction of the reduced form of the soft oxidizing electrophile with the oxidant.

In various embodiments of the invention, when the C—H bond insertion reaction comprises contacting the alkane and a reduced form of the soft oxidizing electrophile plus an oxidant, the reduced form of the soft oxidizing electrophile and the electrophile reduction product can be the identical chemical species. For instance, using the $Bi^{(V)}$(trifluoroacetate), soft oxidizing electrophile embodiment as an example, the soft oxidizing electophile in reduced form can be $Bi^{(III)}$(trifluoroacetate)$_3$ which upon reaction with an oxidant, an oxidizing regeneration reagent, e.g., in trifluoroacetic acid, forms $Bi^{(V)}$(trifluoroacetate), as the reactive electrophilic species, bringing about the alkane functionalization reaction, which yields back $Bi^{(III)}$(trifluoroacetate)$_3$ upon reaction with an alkane, in a cycle of reaction and regeneration.

A soft oxidizing electrophile species $M^nX_n$ can have the following properties: A) good oxidant in the reaction $M^nX_n + 2e^- + 2H^+ \rightarrow M^{(n-2)}X_{n-2} + 2HX$, wherein E° (the standard electrode potential)≤−0.5 V; B) forms relatively strong covalent bonds to carbon; C) is strongly electrophilic; and D) forms relatively weak bonds to the counter anions, X. Species with these characteristics can be described as "soft" oxidizing electrophiles, according to the Pearson hard soft acid base (HSAB) system of classification. The main group metal or non-metal ion, $M^{n+}$, exists in at least two oxidation states $M^{n+}$ and $M^{(n-2)+}$ or $M^{(n-1)+}$, and the number of counterions X to obtain charge neutrality is determined by the value of n. When the reduced form of the main group metal or non-metal ion is in the oxidation state $M^{(n-1)}$, two equivalents of $M^{n+}$ will be required to carry out the alkane oxidation. The standard electrode potential E° of M"X$_n$, can be less than about −0.5 volts, or can be greater than about −1.2 volts. If regeneration of the soft oxidizing electrophile using oxygen as the oxidizing regeneration reagent (second oxidant) is contemplated, the E° standard electrode potential of the MX$_n$ electrophile should be equal to or greater than −1.2 volts, oxygen's E°. It is within ordinary skill to select an MX$_n$ species based on the subject matter disclosed herein, with E° values suitable for the oxidizing regeneration reagent to be used. If stronger oxidants than oxygen are to be used, the E° of the MX$_n$ electrophile can be less than −1.2 volts accordingly.

In some embodiments, the main group metal or non-metal ion M can have only a single pair of oxidation states that meets these criteria, e.g., $Tl^{+3}/Tl^{+1}$, or $Pb^{+4}/Pb^{+2}$, or can have more than a single pair of oxidation states that meet these criteria, e.g., $Bi^{+4}/Bi^{+2}$ and $Bi^{+5}/Bi^{+3}$, or $I^{+7}/I^{+5}$ and $I^{+5}/I^{+3}$ and $I^{+3}/I^{+1}$. In some embodiments, one of the pair of oxidations states can be the zero-valent (elemental) state, but in other embodiments, both of the pair of oxidation states are ionic oxidation states bearing at least a single positive charge. Thus, metal ions having multiple ionization states, such as those of elements Tl, Pb, Bi, and Sb, and non-metal ions such as those of elements Se, Te, and I, can be used.

While not wishing to be bound by theory, the inventors herein believe that a possible unifying feature of some of the MX$_n$ electrophiles useful in carrying out this reaction, such as Tl, Pb, and Bi species, is their isoelectronic configuration in the alkane-reactive oxidation state; the electrons having the configuration [Xe]4f$^{14}$5 d$^{10}$, with an empty 6s orbital. With an unoccupied 6s orbital, having significant spatial distribution near the atomic nucleus, these species are electrophilic and well suited to enter into the formation of carbon-metal bonds in the reaction of the MX$_n$ electrophile with the C—H bond of the alkane substrate. For Sb, there is an unoccupied 5s orbital that can play the same role.

The process of the invention can be carried out in an acidic medium further optionally including an aprotic medium. For example, the medium can be an acidic medium comprising a Bronsted acid, a Lewis acid, or any combination thereof. More specifically, the Bronsted acid can comprise a mineral acid, a carboxylic acid, a sulfonic acid, an aqueous solution thereof, or any combination thereof. For example, the acidic medium can comprise trifluoroacetic, methanesulfonic, or sulfuric acid. The acidic medium can be anhydrous, or can optionally further comprising water, such as aqueous trifluoroacetic acid. The medium can optionally further comprise an aprotic medium, comprising an anhydrous, poorly nucleophilic, liquid capable of dissolving the electrophilic species MX$_n$. An aprotic medium cannot contain water. Examples of suitable aprotic media include liquid sulfur dioxide, trifluoroethanol, tetrachloroethane, or dichloromethane, or a mixture thereof.

The reaction between the alkane and the soft oxidizing electrophile can take place in the absence of a oxidizing regeneration reagent; i.e., the alkane functionalization reaction can be stoichiometric with respect to the electrophile. Accordingly, there is no need to have oxygen or hydrogen peroxide and the hydrocarbon present in a mixture in a single reactor, which can present a safety issue. The soft oxidizing electrophile can be regenerated in a separate step, which can take place sequentially in a reactor, or can take place in a second, parallel, reactor.

In other embodiments, the alkane functionalization reaction can proceed with the soft oxidizing electrophile functioning as a catalyst, with a second oxidant present in the reaction milieu to regenerate the active oxidized form of the electrophile in situ.

The overall reaction, exemplified here in Eq. 4 with a two electron process, can be represented by the reaction sequence wherein the net reaction amounts to a low-temperature, selective, and direct oxidation of the hydrocarbon with molecular oxygen to yield an alcohol:

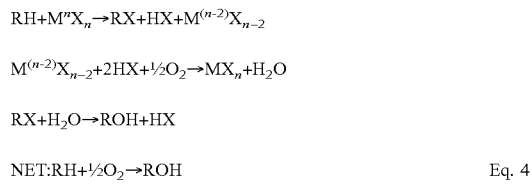

$$\text{NET:} RH + \tfrac{1}{2}O_2 \rightarrow ROH \qquad \text{Eq. 4}$$

In this exemplary scheme, the regenerable soft oxidizing electrophile M"X$_n$ (also termed MX$_n$) undergoes reaction with the alkane to yield a functionalized alkane RX in the reaction of the first equation above. Over-oxidation of methane functionalization products under reaction conditions is a undesired side reaction in many methane functionalization processes, which can result in production of the useless carbon dioxide and unnecessary consumption of the electrophilic species, but is avoided in the presently disclosed processes to a great extent. As discussed above, very little carbon dioxide produced from $^{13}C$ labeled methane was detected in experimental investigations of the reactions with Tl and Pb salts.

As shown in the second reaction above, the reduction product of the soft oxidizing electrophile, $M^{(n-2)}X_{n-2}$, can undergo reaction with an inexpensive oxidizing regeneration species such as $O_2$ or $H_2O_2$ to regenerate the soft oxidizing electrophile species M"X$_n$, in condition for further reaction with the alkane RH. It is also recognized that the oxidation state of the reduced electrophilic species can be (n−1). In this case the first equation above would be replaced by the reaction stoichiometry of $RH + 2M"X_n \rightarrow RX + 2M^{(n-1)}X_{n-1} + HX$.

In the reaction of the third equation above, the functionalized alkane can undergo a hydrolysis reaction with water under suitable conditions to yield the alcohol, ROH, corresponding to the starting alkane, RH. The anion X from the MX$_n$ species is also recovered at this stage. The net reaction is thus oxidation of the alkane to the corresponding alcohol, e.g., methane to methanol, and if the anion X is the conjugate anion of the acid in which the reaction is carried out, e.g., trifluoroacetate, the third reaction provides for regeneration and recycling of this material.

For example, in an embodiment of a method of the invention shown in Eq. 5, wherein the $M^{+n}X$ species is $Tl(CF_3CO_2)_3$ the reaction scheme can be written as:

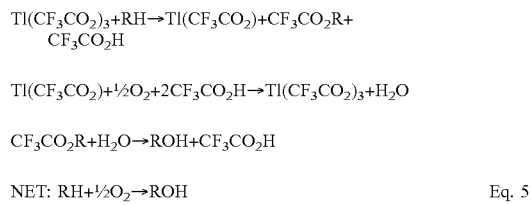

$$\text{NET: } RH + \tfrac{1}{2}O_2 \rightarrow ROH \qquad \text{Eq. 5}$$

In the above reaction sequence, a thallium(III) salt, such as the tris(trifluoroacetate) salt, in an acidic medium, e.g., trifluoroacetic acid, can undergo stoichiometic or catalytic reaction with the alkane to yield the corresponding functionalized alkane, i.e., methyl trifluoroacetate from methane, ethyl trifluoroacetate from ethane, etc. The reduced thallium (I) species, e.g., thallium(I) trifluoroacetate, is also obtained, from which the alkyl trifluoroacetate ester can be separated. In a separate step (ex situ), or in situ, the thallium(I) trifluoroacetate can be oxidized back to thallium(III) tris (trifluoroacetate). Regeneration of this soft oxidizing electrophile can be achieved using oxidants such as $H_2O_2$, chlorine, or elemental oxygen, or with other inexpensive oxidizing agents including, nitric acid, or ozone, and the like, as well as by electrochemical oxidation. The skilled practitioner can select the appropriate oxidant for the specific system.

In another embodiment of a method of the invention shown in Eq. 6, $MX_n$ can be $Pb^{IV}(CF_3CO_2)_4$ where M=Pb, n=4, and $X=CF_3CO_2$. This salt has been shown to react rapidly with various alkanes, RH, in $CF_3CO_2H$ to generate the corresponding oxy-esters, $CF_3CO_2R$ (alkyl trifluoroacetates). This system is more efficient at lower temperatures than the corresponding $Tl^{III}(CF_3CO_2)_3$ example. In this case, the reaction generates the reduced form, $Pb^{II}(CF_3CO_2)_2$. Using hydrogen peroxide ($H_2O_2$) we have been able to regenerate this system so that catalytic amounts of $Pb^{IV}(CF_3CO_2)_4$ can be used.

Pb(IV)(CF$_3$CO$_2$)$_4$+RH→Pb(II)(CF$_3$CO$_2$)$_2$+
CF$_3$CO$_2$R+CF$_3$CO$_2$H

Pb(II)(CF$_3$CO$_2$)$_2$+H$_2$O$_2$+2CF$_3$CO$_2$H→Pb(IV)
(CF$_3$CO$_2$)$_4$+H$_2$O

CF$_3$CO$_2$R+H$_2$O→ROH+CF$_3$CO$_2$H

NET: RH+½O$_2$→ROH   Eq. 6

Regeneration of this soft oxidizing electrophile can be achieved using oxidants such as $H_2O_2$, chlorine, elemental oxygen, or with inexpensive oxidizing agents including, nitric acid, or ozone, and the like, as well as by electrochemically oxidizing the Pb(II) back to the reactive Pb(IV) oxidation state, by applying an oxidative electrochemical potential to the $Pb(II)(CF_3CO_2)_2$. A related half reaction for oxidation of Pb(II) to Pb(IV) is:

PbO+H$_2$O>PbO$_2$+2H$^+$+2e− with E~−1 V.

In another embodiment of a method of the invention shown in Eq. 7, $MX_n$ can be $Bi^V(CF_3CO_2)_3$ where M=Bi, n=3, and $X=CF_3CO_2$. Upon exposure to $H_2O_2$ in situ, this

CF$_3$CO$_2$R+H$_2$O ROH+CF$_3$CO$_2$H

NET: RH+H$_2$O$_2$→ROH+H$_2$O   Eq. 7

In this embodiment, a reduced form of the soft oxidizing electrophile plus an oxidant in situ is used to generate the reactive form of the soft oxidizing electrophile, which undergoes reaction with the alkane.

To determine the effect of catalytic Bi(TFA)$_3$ with H$_2$O$_2$ as the oxidant to oxidize hydrocarbons, we studied the oxidation of ethane gas. This provided use with a relatively unreactive hydrocarbon and can show a selectivity preference for the products and how the catalyst increases the rate of producing products. The selectivity and activity can be used to probe the differences between the oxidant reacting to give product(s) versus the role of the catalyst. An examination of the selectivity for the oxidation of ethane in the absence of Bi(TFA)$_3$ (background) and in the presence of Bi(TFA)$_3$ (catalyzed) was made. The oxidant was consumed in both reactions. However, the selectivity differences were quite significant as the background shows EtTFA, and AcOH as the major products with trace levels of EG(TFA)$_2$ and MeTFA. Whereas, in the presence of the Bi(TFA)$_3$, The products are almost exclusively EtTFA with trace levels of MeTFA and AcOH. This system is more efficient at much lower temperatures than the corresponding $Tl^{III}(CF_3CO_2)_3$ or $Pb^{IV}(CF_3CO_2)_4$ examples.

The Bi(TFA)3 greatly changes the selectivity of the oxidation of ethane with H$_2$O$_2$, it is important to also understand the differences in rate between the background and catalyzed reaction. However, to observe this requires lowering the reaction temperature from 180° C. to 80° C. Under these reaction conditions, even after 1 hour, the catalyzed reaction achieves 75% yield and the uncatalyzed reaction is <5% yield.

Table 3 provides experimental results obtained by use of the $Bi^{III}/H_2O_2$ system.

TABLE 3

Oxidation of ethane with H$_2$O$_2$ catalyzed by Bi(TFA)$_3$.
Standard conditions: 25 mM Bi(TFA)$_3$, 500 mM H$_2$O$_2$, 500 psig EtH,
1.75 ml HTFA, 0.22 ml TFAA (removes water from 50% H$_2$O$_2$ solution).

| Oxidant | Conc (M) | Hydrocarbon | T (° C.) | Time (h) | Products (% of Total products) | Analysis | TON | Yield (Based on Ox) |
|---|---|---|---|---|---|---|---|---|
| H$_2$O$_2$ | 0.5 | EtH | 180 | 1 | EtTFA(97%),MeTFA (1%), AcOH (2%) | $^1$H-NMR | 16 | 80% |
| H$_2$O$_2$ | 0.5 | EtH | 80 | 1 | EtTFA(92%),MeTFA (2%), AcOH (6%) | $^1$H-NMR | 15 | 75% |
| NaBO$_3$ | 0.5 | EtH | 180 | 1 | EtTFA(92%),MeTFA (2%), AcOH (6%) | $^1$H-NMR | 16 | 80% | salt can catalytically react rapidly with various alkanes, RH, in CF$_3$CO$_2$H to generate the corresponding oxy-esters, CF$_3$CO$_2$R.

Bi(CF$_3$CO$_2$)$_3$+H$_2$O$_2$+2CF$_3$CO$_2$H→Bi(CF$_3$CO$_2$)$_5$+
H$_2$O

Bi(CF$_3$CO$_2$)$_5$+RH→Bi(CF$_3$CO$_2$)$_3$+CF$_3$CO$_2$R+
CF$_3$CO$_2$H

It can be possible to regenerate this catalyst using oxidants other than H$_2$O$_2$ such a chlorine, elemental oxygen, and the like, as well as by electrochemically oxidizing the Bi(III) back to the reactive Bi(V) oxidation state, by applying an oxidative electrochemical potential to the Bi(III) (CF$_3$CO$_2$)$_3$.

In yet another embodiment of a method of the invention, $MX_n$ can be an $I^{+3}$ salt such as $I^{(III)}(CF_3CO_2)_3$ where M=I, n=3, and X=CF$_3$CO$_2$. This salt has been shown to catalytically react rapidly with various alkanes, RH, in CF$_3$CO$_2$H to generate the corresponding oxy-esters, CF$_3$CO$_2$R. In other embodiments, the MX$_n$ species can be a salt of Se(VI), i.e., Se$^{+6}$, or of Te(VI), i.e., Te$^{+6}$, or of I(V), i.e., I$^{+5}$.

While the species MX$_n$ is referred to herein as a "salt", it is understood that there may be a significant amount of covalent bonding between the M atoms and the X moieties, depending upon the exact identify of the MX$_n$ material used. In the embodiments using selenium, tellurium, or iodine, the species MX$_n$ likely has very considerable covalent character.

It can be possible to regenerate this soft oxidizing electrophile using oxidants other than H$_2$O$_2$ such a chlorine, elemental oxygen, and the like, as well as by electrochemically oxidizing the reduced I, Se, and Te species back to their reactive the I(III), I(V), Se(VI), or Te(VI) oxidation states, by applying an oxidative electrochemical potential to the electrophile reduction product.

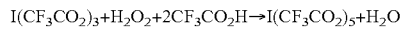

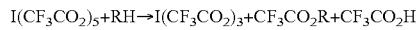

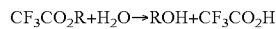

This reaction set can also apply to the reactions with the selenium and tellurium reagents as well, in that the more oxidized form of the reagent, i.e., the soft oxidizing electrophile, inserts into the C—H bond of the alkane, with an internal oxidation-reduction reaction taking place to reduce the iodine, selenium, or tellurium atom, in conjunction with formation of a bond between the alkyl group and the trifluoroacetic acid reaction milieu. Table 4 provides data relating to the use of iodine, selenium, and tellurium oxidizing electrophiles.

In various embodiments, the invention is directed to processes involving the utilization of selenium, tellurium and hypervalent iodine reagents including iodates, including, but not limited to, Te(OH)$_6$, H$_2$SeO$_4$, I(OTFA)$_3$, Ph-I(OTFA)$_2$, C$_6$F$_5$—I(OTFA)$_2$, KIO$_3$ and HIO$_3$ to affect the selective conversion of primary feedstock hydrocarbons including, but not limited to, methane, ethane, propane, and benzene, to functionalized alkane products including, but not limited to, methanol, ethanol, ethylene glycol, propanols, propylene glycols, and phenol. For instance, we have begun to systematically study the reactivity of strongly electrophilic main-group electrophiles towards light alkanes. Hypervalent iodine reagents (I$^{III}$, I$^V$, I$^{VII}$) are relatively non-toxic, strong electrophiles which have been extensively developed in the past 30 yrs for a wide variety of oxidative organic transformations; with recent advances employing iodine catalytically. Furthermore, to our knowledge only one system (which operates in super-acid media) describes the selective and high yielding oxy-functionalization of a C$_1$-C$_3$ alkane (methane),[48] with no reports concerning ethane and propane. Herein, we describe our work on the homogeneous stoichiometric oxy-functionalization of C$_1$-C$_3$ alkanes by the well-defined hypervalent iodine compound C$_6$F$_5$—I$^{III}$(TFA)$_2$. Studies show that in trifluoroacetic acid (HTFA) media, C$_6$F$_5$—I$^{III}$(TFA)$_2$ cleanly and selectively oxidizes C$_1$-C$_3$ alkanes (RH) to generate the respective trifluoroacetate esters (R-TFA) and C$_6$F$_5$—I$^1$, in high yields for ethane and propane.

Heating a 100 mM solution of C$_6$F$_5$—I$^{III}$(TFA)$_2$ at 150° C. for 3 hrs in 100 mM TFAA/HTFA under 500 psi of methane or ethane (125 psi for PrH) was shown by the $^1$H-NMR of the crude reaction mixtures to generate the respective trifluoroacetate (TFA) mono-esters and 1,2-TFA-diesters (for EtH and PrH) as shown in Eq. 9:

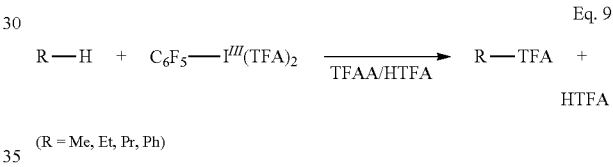

(R = Me, Et, Pr, Ph)

The reactions are highly selective and no hydrocarbon derived products are observed besides the respective mono- and 1,2-di-esters (Table 5). $^{19}$F-NMR analysis of the solutions post-reaction showed that C$_6$F$_5$—I$^{III}$(TFA)$_2$ is converted to C$_6$F$_5$—I$^I$, as the reaction proceeds with no intermediate iodine species observed.

TABLE 4

Conversions of Unactivated Hydrocarbons with Iodine, Selenium, and Tellurium Reagents

| Entry | Oxidant | Conc (M) | Solvent | Hydrocarbon | T (° C.) | Time (h) | Products (% of Total products) | Analysis | Yield (Based on Ox) |
|---|---|---|---|---|---|---|---|---|---|
| 1 | I(OTFA)$_3$ | 0.3 | HTFA | MeH | 150 | 3 | MeTFA (100%) | $^1$H-NMR | 5% |
| 2 | " | 0.3 | HTFA | EtH | 150 | 3 | EtTFA (90%), EG(TFA)2 (10%) | $^1$H-NMR | 22% |
| 3 | " | 0.3 | HTFA | PrH | 150 | 3 | iPrTFA (>97%) | $^1$H-NMR | 32% |
| 4 | " | 0.3 | HTFA | PrH | 180 | 3 | iPrTFA (80%), 1,2-PrG (20%) | $^1$H-NMR | 54% |
| 5 | C$_6$F$_5$—I(OTFA)$_2$ | 0.1 | HTFA | PrH | 140 | 3 | iPrTFA (85%), 1,2-PrG (15%) | $^1$H-NMR and $^{19}$F-NMR | 44% |
| 6 | " | 0.25 | HTFA | C$_6$H$_6$ | 50 | 3 | Ph-TFA (100%) | $^1$H-NMR and $^{19}$F-NMR | 16% |
| 7 | " | 0.25 | HTFA | C$_6$H$_6$ | 75 | 3 | Ph-TFA (100%) | $^1$H-NMR and $^{19}$F-NMR | 28% |
| 8 | " | 0.25 | HTFA | C$_6$H$_6$ | 100 | 3 | Ph-TFA (100%) | $^1$H-NMR and $^{19}$F-NMR | >99% |
| 9 | HIO$_3$ | 0.25 | TFA$_2$O/HTFA | EtH | 150 | 3 | EtTFA (93%), EG(TFA)2 (6%), AcOH (1%) | $^1$H-NMR | 234% |
| 10 | " | 0.025 | TFA$_2$O/HTFA | EtH | 150 | 3 | EtTFA (50%), AcOH (50%) | $^1$H-NMR | 180% |
| 11 | HIO$_3$ + O$_2$ | 0.025 | TFA$_2$O/HTFA | EtH | 150 | 3 | EtTFA (32%), CH$_3$—CH(TFA)$_2$ (43%), AcOH (25%) | $^1$H-NMR | 750% |
| 12 | Te(OH)$_6$ | 0.25 | TFA$_2$O/HTFA | MeH | 180 | 3 | "Te—Me" (~100%) | $^1$H-NMR-Used $^{13}$CH$_4$ | >90% |
| 13 | H$_2$SeO$_4$ | 0.25 | TFA$_2$O/HTFA | MeH | 180 | 3 | MeTFA (10%), "Se—Me" (13%), Other (77%) | $^1$H-NMR | <10% |
| 14 | " | 0.25 | TFA$_2$O/HTFA | EtH | 180 | 3 | EtTFA(82%), EG(TFA)$_2$ (2%), CH3—C(TFA)$_2$H (15%) | $^1$H-NMR | 23% |

TABLE 5

Oxidation of $C_1$-$C_3$ alkanes and benzene by $C_6F_5$—$I^{III}$(TFA)$_2$

| Entry | RH | T (° C.) | % Conv. | Product(s), (Yield) |
|---|---|---|---|---|
| 1 | MeH | 150 | 5% | MeTFA (5%, 5 mM) |
| 2 | EtH | 150 | 80% | EtTFA (73%, 73 mM); 1,2-Et(TFA)$_2$ (3%, 3 mM) |
| 3[c] | PrH | 150 | 89% | 2-PrTFA (30%, 30 mM); 1,2-Pr(TFA)$_2$ (27%, 27 mM) |
| 4[d] | EtH | 150 | 88% | EtTFA (72%, 565 mM); 1,2-Et(TFA)$_2$ (8%, 61 mM) |
| 5[e] | $C_6H_6$ | 125 | 99% | $C_6H_5$TFA (91%, 228 mM) |
| 6[e] | $C_6H_6$ | 100 | 99% | [$C_6F_5$—$I^{III}$—$C_6H_5$][TFA] (99%, 247 mM) |

[a] General Reaction Conditions: 100 mM C6F5—I(TFA)2, 1 mL 100 mM TFAA/HTFA, 3 hrs, 500 psi RH.
[b] Conversion and product yields were determined via $^{19}$F- and $^1$H-NMR respectively, by comparison to an internal standard (C$_6$F$_6$ and CH$_2$Cl$_2$) which was added post reaction.
[c]115 psi PrH.
[d]0.78M C6F5—I(TFA)2.
[e]690 mM C$_6$H$_6$, 250 mM C6F5—I(TFA)2, 500 psi Ar.

Control experiments showed that $C_6F_5$—$I^{III}$(TFA)$_2$ was stable under the reaction conditions (under 500 psi Ar) in the absence of the hydrocarbons; and that the hydrocarbons did not react in the absence of $C_6F_5$—$I^{III}$(TFA)$_2$. Consistent with the expected relative reactivities of the hydrocarbons, the order of reactivity was determined to be propane (~90%)>ethane (80%)>>methane (5%) (Table 5, Entries 1-3). The reaction was highly efficient with EtH and PrH; and at the saturation concentration of $C_6F_5$—$I^{III}$(TFA)$_2$ (~0.8 M), 0.56 M EtTFA could be observed (Table 5, Entry 4).

Notably, the selectivity for the mono- and 1,2-difunctionalized products depended upon substrate: the mono ester is heavily favored (24:1) for ethane; while a 1:1 ratio is observed for propane. Control experiments suggest that this difference likely arises due to the relative reactivities of the mono-ester products: 2-PrTFA is readily converted into 1,2-Pr(TFA)$_2$ under our standard reaction conditions, while EtTFA is completely unreactive towards $C_6F_5$—$I^{III}$(TFA)$_2$.

To recover the final equivalent of trifluoroacetate in any of the above embodiments, e.g., for recycle in the process, the alkyl trifluoroacetate ester can undergo hydrolysis with water under suitable conditions to yield the alcohol, i.e., methanol from methane, ethanol from ethane, etc.

In yet other embodiments, the RX, or R-MX$_n$ species can undergo a reaction other than hydrolysis with water providing an alcohol; e.g., reaction with a carboxylic acid can by transesterification to yield a different ester of the alcohol than the, e.g., trifluoroacetyl ester obtained directly.

As in other embodiments, the process can further comprise contacting the electrophile reduction product and an oxidizing regeneration reagent, appropriately selected by the skilled practitioner, to regenerate the soft oxidizing electrophile.

Figure 3:
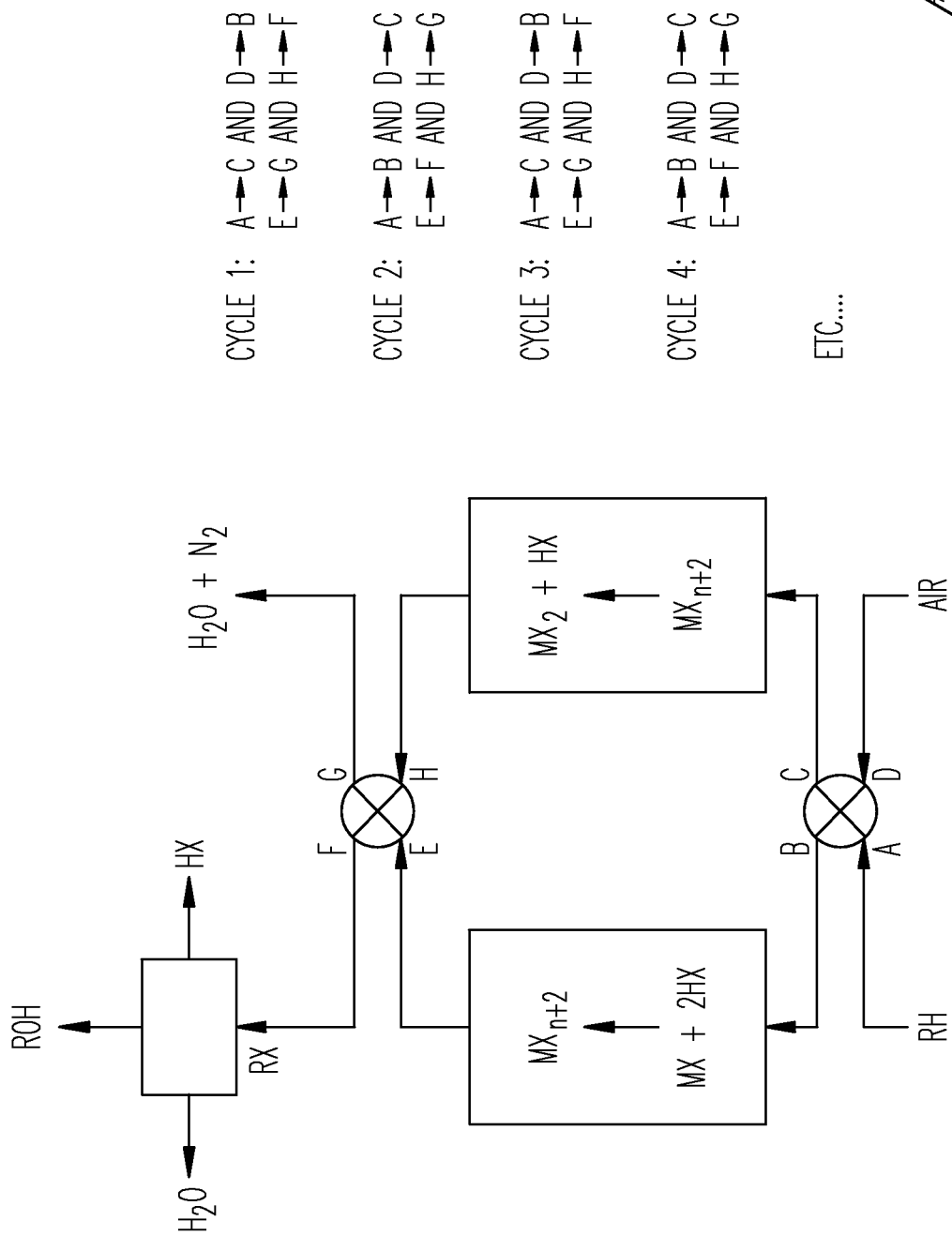
FIG. 3 shows a simplified process diagram for the conversion of hydrocarbons (RH) to the corresponding alcohol (ROH) using $MX_n$ as the air recyclable stoichiometric oxidants in a switching reactor system that can continuously generate products.
Figure 4:
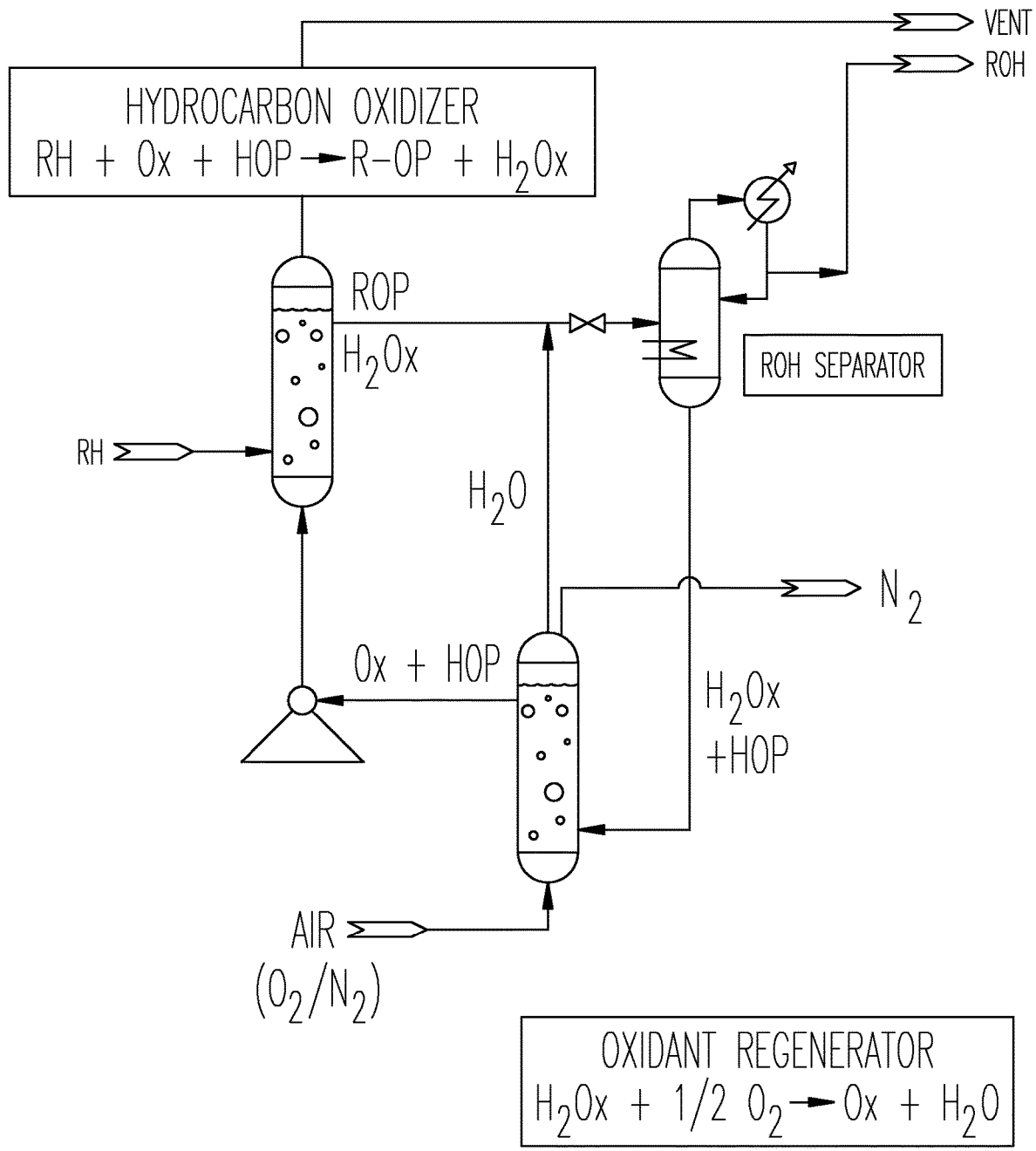
FIG. 4 shows a simplified process flow diagram for the continuous partial oxidation of alkanes, RH, with air to the corresponding alcohols, ROH.

In various embodiments, the functionalized alkane RX and the electrophile reduction product $M^{(n-2)}X_{n-2}$ can then be separated by means known in the art, e.g., distillation, evaporation, or extraction. The desired reaction product RX can then be used directly, purified, or converted to other chemical species as desired. The electrophile reduction product $M^{(n-2)}X_{n-2}$ can then be reoxidized in a regeneration step. Examples of different reactor systems that can be used to accomplish this sequence are described in more detail below, but can include a switched parallel pair of reactors, sequential operation of the two steps in the same reaction, and the like. For example, the soft oxidizing electrophile reagent can be immobilized, e.g., on an ion exchange resin or the like, allowing flow through by reagents in the hydrocarbon activation step, followed by regeneration of the oxidizing electrophile. See FIGS. 3 and 4.

In regeneration of the soft oxidizing electrophile $M^{+n}X_n$ from the electrophile reduction product $M^{(n-2)}X_{n-2}$ that results from reaction with the alkane, the electrophile reduction product is reacted with an oxidizing regeneration reagent, optionally in the presence of a regeneration catalyst for example copper ions can be used as shown in Eq. 10:

$$2CuX + \tfrac{1}{2}O_2 + 2HX \rightarrow 2CuX_2 + H_2O$$

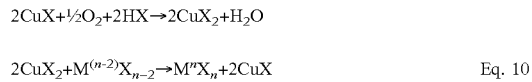

$$2CuX_2 + M^{(n-2)}X_{n-2} \rightarrow M^nX_n + 2CuX \qquad \text{Eq. 10}$$

In this example, oxygen serves as the ultimate oxidant, as the copper species is regenerated by oxygen, after re-oxidation of the $M^{(n-2)}X_{n-2}$ species to yield the soft oxidizing electrophile $M^nX_n$. Other elements can serve as catalysts for the reaction of the regenerating oxidant and the reduced electrophile, such as silver, iron, or vanadium. However, the regeneration of the soft oxidizing electrophile can be carried out using only an oxidant, e.g., oxygen, without any requirement for the presence of a catalyst.

The process of reacting the alkane and the soft oxidizing electrophile can be carried out in a single reactor, sequentially. Thus, the reactor can be operated first under conditions suitable for the reaction of the alkane and the soft oxidizing electrophile, then under conditions suitable for regeneration of the soft oxidizing electrophile by contacting the electrophile reduction product and the oxidizing regeneration species. For example, the electrophile can be immobilized within the reactor, wherein first a mixture comprising the hydrocarbon substrate is circulated, then, when the oxidizing electrophile is depleted, a mixture comprising the oxidizing regeneration species, such as oxygen, optionally in the presence of a catalyst, is circulated to regenerate the reactive form of the soft oxidizing electrophile, such as the metal composition $MX_n$. While the species $MX_n$ is referred to herein as a metal "salt", it is understood that there may be a significant amount of covalent bonding between the M atoms and the X moieties, depending upon the exact identify of the $MX_n$ material used. Thus, an $MX_n$ such as Tl(CF$_3$CO$_2$)$_3$ $_3$ is referred to herein at times as a "salt", although there may be considerable covalent in addition to ionic nature in the CF$_3$C(O)O—Tl bond. The $MX_n$ soft oxidizing electrophile can be present in solution in the reactor, as a solid, e.g., in a fluidized bed reactor, or bound to a solid phase, such as an ion exchange resin or a solid polymer bearing metal chelating groups.

In other embodiments, the process can be carried out in a two reactor circulating liquid phase system, wherein the reaction of the alkane and the soft oxidizing electrophile is carried out in a first reactor and the reaction of the electrophile reduction product and the oxidant species to regenerate the soft oxidizing electrophile is carried out in a second reactor.

The inventors believe that the process schemes disclosed and claimed herein can enable the direct conversion of alkanes (RH) and air (N$_2$/O$_2$) to the corresponding alcohols (ROH) at temperatures below 300° C., with high volumetric productivity (10$^{-6}$ mol/cc-sec), alkane conversions (>90%) and ROH selectivity (>90%).

In addition to mono alcohols the diols of ethane and propane can also generated. These routes for the direct conversion of the alkanes to these products can be expected to lead to much lower costs for the production of materials. Our initial results suggest that the diols are not generated from the mono-alcohols, but from a common M-R intermediate. This would suggest that under the appropriate reaction conditions reactions could be optimized for the mono or di-alcohols.

The process can be carried out in a single reactor, sequentially. Thus, the reactor can be operated first under conditions suitable for the reaction of the alkane and the soft oxidizing electrophile, then under conditions suitable for regeneration of the soft oxidizing electrophile by contacting the electrophile reduction product and the oxidizing regeneration species. For example, the electrophile can be immobilized within the reactor, wherein first a mixture comprising the hydrocarbon substrate is circulated, then, when the oxidizing electrophile is depleted, a mixture comprising the oxidizing regeneration species, such as oxygen, optionally in the presence of a catalyst, is circulated to regenerate the reactive form of the soft oxidizing electrophile, such as the metal composition $MX_n$. While the species $MX_n$ is referred to herein as a metal "salt", it is understood that there may be a significant amount of covalent bonding between the M atoms and the X moieties, depending upon the exact identify of the $MX_n$ material used. Thus, an $MX_n$ such as Bi(V) $(CF_3CO_2)_5$, is referred to herein at times as a "salt", although there may be considerable covalent in addition to ionic nature in the $CF_3C(O)O$—Bi bond. The $Bi(V)(CF_3CO_2)_5$, soft oxidizing electrophile can be present in solution in the reactor, as a solid, e.g., in a fluidized bed reactor, or bound to a solid phase, such as an ion exchange resin or a solid polymer bearing metal chelating groups.

In other embodiments, the process can be carried out in a two reactor circulating liquid phase system, wherein the reaction of the alkane and the soft oxidizing electrophile is carried out in a first reactor and the reaction of the electrophile reduction product and the oxidant species to regenerate the soft oxidizing electrophile is carried out in a second reactor.

In addition to mono alcohols the diols of ethane and propane can also generated. These routes for the direct conversion of the alkanes to these products can be expected to lead to much lower costs for the production of materials. Our initial results suggest that the diols are generated from the mono-alcohols. This would suggest that under the appropriate reaction conditions reactions could be optimized for the mono or di-alcohols.

DOCUMENTS CITED

1. U. S. E. I. Administration, "U.S. Crude Oil and Natural Gas Proved Reserves, 2011," (1-49) (2013).
2. D. L. George, E. B. Bowles, Jr., *Pipeline & Gas Journal* 238, 38-41 (2011).
3. N. F. Gol'dshleger, V. V. Es'kova, A. A. Shteinman, A. E. Shilov, *Russ J Phys Ch Ussr* 46, 785-786 (1972).
4. A. E. Shilov, A. A. Shteinman, *Coordin Chem Rev* 24, 97-143 (1977).
5. A. Sen, *Accounts Chem Res* 31, 550-557 (1998).
6. M. J. Burk, R. H. Crabtree, C. P. Parnell, R. J. Uriarte, *Organometallics* 3, 816-817 (1984).
7. M. J. Burk, R. H. Crabtree, *J Am Chem Soc* 109, 8025-8032 (1987).
8. M. C. Haibach, S. Kundu, M. Brookhart, A. S. Goldman, *Accounts Chem Res* 45, 947-958 (2012).
9. J. Choi, A. H. R. MacArthur, M. Brookhart, A. S. Goldman, *Chem Rev* 111, 1761-1779 (2011).
10. A. S. Goldman, A. H. Roy, Z. Huang, R. Ahuja, W. Schinski, M. Brookhart, *Science* 312, 257-261 (2006).
11. B. G. Hashiguchi, S. M. Bischof, M. M. Konnick, R. A. Periana, *Accounts Chem Res* 45, 885-898 (2012).
12. C. J. Jones, D. Taube, V. R. Ziatdinov, R. A. Periana, R. J. Nielsen, J. Oxgaard, W. A. Goddard, *Angew Chem Int Edit* 43, 4626-4629 (2004).
13. R. A. Periana, O. Mirinov, D. J. Taube, S. Gamble, *Chem Commun*, 2376-2377 (2002).
14. R. A. Periana, O. Mironov, D. Taube, G. Bhalla, C. J. Jones, *Science* 301, 814-818 (2003).
15. R. A. Periana, D. J. Taube, E. R. Evitt, D. G. Loffler, P. R. Wentrcek, G. Voss, T. Masuda, *Science* 259, 340-343 (1993); see also published PCT application WO92/14738.
16. R. A. Periana, D. J. Taube, S. Gamble, H. Taube, T. Satoh, H. Fujii, *Science* 280, 560-564 (1998).
17. M. Muehlhofer, T. Strassner, W. A. Herrmann, *Angew Chem Int Edit* 41, 1745-1747 (2002).
18. T. Strassner, M. Muehlhofer, A. Zeller, E. Herdtweck, W. A. Herrmann, *J Organomet Chem* 689, 1418-1424 (2004).
19. S. Ahrens, A. Zeller, M. Taige, T. Strassner, *Organometallics* 25, 5409-5415 (2006).
20. J. F. Hartwig, *Accounts Chem Res* 45, 864-873 (2012).
21. J. F. Hartwig, K. S. Cook, M. Hapke, C. D. Incarvito, Y. B. Fan, C. E. Webster, M. B. Hall, *J Am Chem Soc* 127, 2538-2552 (2005).
22. H. Chen, S. Schlecht, T. C. Semple, J. F. Hartwig, *Science* 287, 1995-1997 (2000).
23. Z. J. An, X. L. Pan, X. M. Liu, X. W. Han, X. H. Bao, *J Am Chem Soc* 128, 16028-16029 (2006).
24. G. J. Hutchings, M. S. Scurrell, J. R. Woodhouse, *Chem Soc Rev* 18, 251-283 (1989).
25. C. Hammond, M. M. Forde, M. H. Ab Rahim, A. Thetford, Q. He, R. L. Jenkins, N. Dimitratos, J. A. Lopez-Sanchez, N. F. Dummer, D. M. Murphy, A. F. Carley, S. H. Taylor, D. J. Willock, E. E. Stangland, J. Kang, H. Hagen, C. J. Kiely, G. J. Hutchings, *Angew Chem Int Edit* 51, 5129-5133 (2012).
26. P. Vanelderen, J. Vancauwenbergh, B. F. Sels, R. A. Schoonheydt, *Coordin Chem Rev* 257, 483-494 (2013).
27. M. N. Vargaftik, I. P. Stolarov, I. I. Moiseev, *J Chem Soc Chem Comm*, 1049-1050 (1990).
28. I. P. Stolarov, M. N. Vargaftik, D. I. Shishkin, I. I. Moiseev, *J Chem Soc Chem Comm*, 938-939 (1991).
29. A. J. Bard, R. Parsons, J. Jordan, *Standard Potentials in Aqueous Solution*. (International Union of Pure and Applied Chemistry, New York, N. Y., 1985).
30. M. Ahlquist, R. A. Periana, W. A. Goddard, *Chem Commun*, 2373-2375 (2009).
31. F. Basolo, R. G. Pearson, *Mechanisms of Inorganic Reactions*. (Wiley, ed. 2nd, 1967).
32. R. G. Peterson, *Hard and soft acids and bases*. (Dowden, Hutchinson and Ross, Inc., Stroudsburg, P A, 1973).
33. H. Kurosawa, R. Okawara, *J Organomet Chem* 10, 211-217 (1967).
34. T. Fujii, K. Funahashi, I. Hirose, U.S. Pat. No. 3,399,956 (1968)
35. R. A. Johnson, U.S. Pat. No. 4,113,756 (1978)
36. R. A. Johnson, U.S. Pat. No. 4,192,814 (1980)
37. A. Mckillop, J. D. Hunt, M. J. Zelesko, J. S. Fowler, E. C. Taylor, Mcgilliv. G, F. Kienzle, *J Am Chem Soc* 93, 4841-4844 (1971).
38. H. C. Bell, J. R. Kalman, J. T. Pinhey, S. Sternhell, *Aust J Chem* 32, 1521-1530 (1979).
39. I. E. Marko, J. M. Southern, *J Org Chem* 55, 3368-3370 (1990).
40. F. Brady, R. W. Matthews, M. M. Thakur, D. G. Gillies, *J Organomet Chem* 252, 1-27 (1983).
41. Gaussian 09, Revision B.01, M. J. Frisch, G. W. Trucks, H. B. Schlegel, G. E. Scuseria, M. A. Robb, J. R. Cheeseman, G. Scalmani, V. Barone, B. Menucci, G. A.

Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomassi, M. Cossi, N. Rega, N. J. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, D. J. Fox, Gaussian, Inc., Wallingford Conn., (2009).
42. Y. Zhao, D. G. Truhlar, *Theor Chem Acc* 120, 215-241 (2008).
43. Y. Zhao, D. G. Truhlar, *Accounts Chem Res* 41, 157-167 (2008).
44. A. V. Marenich, C. J. Cramer, D. G. Truhlar, *J Phys Chem B* 113, 6378-6396 (2009).
45. J. G. Speight, *Lange's Handbook of Chemistry*. (McGraw-Hill, New York, 2005).
46. M. J. O'Neil, S. Budavari. (Merck, Whitehouse Station, N J, 2001).
47. J. B. Milne, T. J. Parker, *J. Solution Chem.* 10, 479-487 (1981).
48. a) R. A. Periana, O. Mirinov, D. J. Taube, S. Gamble, *Chem. Commun.* 2002, 2376; b) X. Gang, Y. Zhu, H. Birch, H. A. Hjuler, N. J. Bjerrum, *App. Cat. A: Gen.* 2004, 261, 91; c) B. Michalkiewicz, M. Jarosinska, I. Lukasiewicz, *Chem. Eng. J.* 2009, 154, 156.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for oxidizing an alkane to an alkane oxygenate, comprising contacting the alkane and
   (i) a soft oxidizing electrophile comprising a main group element selected from the group consisting of gallium, germanium, arsenic, selenium, indium, tin, antimony, tellurium, thallium, and bismuth in oxidized form, or
   (ii) an oxidant and a reduced form of the soft oxidizing electrophile to provide the soft oxidizing electrophile comprising a main group element selected from the group consisting of gallium, germanium, arsenic, selenium, indium, tin, antimony, tellurium, thallium, and bismuth in oxidized form,
   in an acidic medium comprising an oxygen acid, in the absence of a super-acid wherein the super-acid is an acid with an acidity greater than or equal to that of concentrated sulfuric acid, to provide, without the need for molecular oxygen, the alkane oxygenate and an electrophile reduction product; and
   optionally separating the alkane oxygenate and the electrophile reduction product, wherein
   the soft oxidizing electrophile is present in at least stoichiometric quantities relative to the alkane converted to oxygenated products in the acidic medium.

2. The process of claim 1, further comprising contacting the electrophile reduction product and an oxidizing regeneration reagent to regenerate the soft oxidizing electrophile.

3. The process of claim 2, wherein the oxidizing regeneration reagent is molecular oxygen, hydrogen peroxide, chlorine, nitric acid, or ozone.

4. The process of claim 2, wherein the electrophile reduction product and the oxidizing regeneration reagent are contacted to regenerate the soft oxidizing electrophile in the presence of an oxidative regeneration catalyst.

5. The process of claim 4, wherein the oxidative regeneration catalyst comprises copper, silver, iron, or vanadium.

6. The process of claim 2, wherein the oxidizing regeneration reagent is present in at least stoichiometric quantities relative to the alkane, in the acidic medium with the soft oxidizing electrophile, and wherein the oxidizing regeneration reagent oxidizes the electrophile reduction product to the soft oxidizing electrophile in the acidic medium in the presence of the alkane.

7. The process of claim 1, wherein the soft oxidizing electrophile comprises thallium, antimony, selenium, tellurium, or bismuth, each in oxidized form.

8. The process of claim 1, wherein the soft oxidizing electrophile comprises one or more trifluoroacetate, acetate, sulfate, or alkylsulfonate anions.

9. The process of claim 1, wherein the alkane is methane, ethane, or propane, or any mixture thereof.

10. The process of claim 1, wherein the soft oxidizing electrophile comprising a main group element in oxidized form is a salt wherein the counterion of the main group element in oxidized form is a conjugate anion of an acid of the acidic medium.

11. The process of claim 10, wherein the acidic medium comprises trifluoroacetic acid, acetic acid, or methanesulfonic acid, and the counterion of main group element in oxidized form is trifluoroacetate, acetate, or methanesulfonate, respectively.

12. The process of claim 1, wherein the soft oxidizing electrophile has the formula $M^{+n}X_n$, wherein M is a metal or non-metal main group element cation in an oxidation state of n, X is an anionic counterion, and n is the number of anionic charges necessary to balance the n+ positive charge of the metal ion.

13. The process of claim 12, wherein $M^{+n}X_n$ undergoes reaction with the alkane in the acidic medium to yield an electrophile reduction product of formula $M^{+(n-2)}X_{n-2}$ or $M^{+(n-1)}X_{n-1}$.

14. The process of claim 1, wherein the medium further comprises an aprotic medium, comprising an anhydrous, poorly nucleophilic, polar liquid.

15. The process of claim 14, wherein the aprotic medium is liquid sulfur dioxide, trifluoroethanol, tetrachloroethane, or dichloromethane, or a mixture thereof.

16. The process of claim 1, wherein the soft oxidizing electrophile comprising a main group element in oxidized form is present in less than stoichiometric quantities relative to the alkane and acts as a catalyst.

17. The process of claim 1, wherein no oxidizing regeneration reagent is present in the acidic medium with the soft oxidizing electrophile comprising a main group element in oxidized form, and the soft oxidizing electrophile is present in at least stoichiometric quantities relative to the alkane converted to oxygenated products in the acidic medium.

18. The process of claim 1, comprising separating the alkane oxygenate and the electrophile reduction product.

19. The process of claim 1, when the alkane is other than methane, the alkane oxygenate comprises a diol, a diol monoester, a diester, or a combination thereof.

20. The process of claim 1, wherein the process takes place at a temperature of less than 300° C.

21. The process of claim 20, comprising separating the alkane oxygenate and the electrophile reduction product.

* * * * *